(12) United States Patent
Tanaka et al.

(10) Patent No.: US 7,960,363 B2
(45) Date of Patent: Jun. 14, 2011

(54) THERAPEUTIC AGENT FOR WOUNDS AND SCREENING METHOD FOR THE SAME

(75) Inventors: Takashi Tanaka, Kanagawa (JP); Tsuneyasu Kaisho, Kanagawa (JP)

(73) Assignee: RIKEN, Wako-shi (JP)

( * ) Notice: Subject to any disclaimer, the term of this patent is extended or adjusted under 35 U.S.C. 154(b) by 0 days.

(21) Appl. No.: 12/613,134

(22) Filed: Nov. 5, 2009

(65) Prior Publication Data

US 2010/0280095 A1   Nov. 4, 2010

(30) Foreign Application Priority Data

May 1, 2009   (JP) ................................ 2009-112250

(51) Int. Cl.
*A61K 48/00*   (2006.01)
(52) U.S. Cl. ...... 514/44; 536/24.31; 536/24.1; 536/24.5
(58) Field of Classification Search .................. None
See application file for complete search history.

(56) References Cited

U.S. PATENT DOCUMENTS

2006/0177906 A1 *   8/2006   O'Connor et al. ........... 435/69.1
2006/0246543 A1   11/2006   Grusby et al.

FOREIGN PATENT DOCUMENTS

JP   2007-254465 A   10/2007

OTHER PUBLICATIONS

Soutschek et al. Therapeutic silencing of an endogenous gene by systemic administration of modified siRNAs. Nature vol. 432, 2004 oo:173-178.*
Tanaka et al., *Immunity*, 22: 729-736 (Jun. 2005).
Tanaka et al., *Nature Immunology*, 8(6): 584-591 (Jun. 2007).

* cited by examiner

*Primary Examiner* — Kimberly Chong
(74) *Attorney, Agent, or Firm* — Leydig, Voit & Mayer, Ltd.

(57) ABSTRACT

The present invention provides an agent for treating wound, containing a substance that suppresses the expression or function of PDLIM2. The substance that suppresses the expression or function of PDLIM2 is preferably an siRNA or antisense nucleic acid capable of specifically suppressing the expression of PDLIM2, or an expression vector capable of expressing said polynucleotide. In addition, the present invention provides a method of screening for a substance capable of treating wounds, including determining whether or not a test substance is capable of suppressing the expression or function of PDLIM2.

7 Claims, 8 Drawing Sheets (a)

(c)

(b)

(d)

(a)

(b)

(a)

(b)

(c)

(a)

(b)

(c)

(d)

7 days after injury

SEQUENCE LISTING

<160> NUMBER OF SEQ ID NOS: 8

<210> SEQ ID NO 1
<211> LENGTH: 4611
<212> TYPE: DNA
<213> ORGANISM: Homo sapiens
<220> FEATURE:
<221> NAME/KEY: CDS
<222> LOCATION: (135)..(1235)

<400> SEQUENCE: 1

```
aagcccctga gtagctgctc cgggagctgt ggtgccctct ccttctccct ttggctcctc      60
tcctgctgcc ttacagtgcc cccagagccg gctaggggca tggacttcac ctcctggtcc     120
tctcttcctc aggt atg gcg ttg acg gtg gat gtg gcc ggg cca gcg ccc      170
             Met Ala Leu Thr Val Asp Val Ala Gly Pro Ala Pro
              1               5                  10 tgg ggc ttc cgt atc aca ggg ggc agg gat ttc cac acg ccc atc atg      218
Trp Gly Phe Arg Ile Thr Gly Gly Arg Asp Phe His Thr Pro Ile Met
             15                  20                  25 gtg act aag gtg gcc gag cgg ggc aaa gcc aag gac gct gac ctc cgg      266
Val Thr Lys Val Ala Glu Arg Gly Lys Ala Lys Asp Ala Asp Leu Arg
 30                  35                  40 cct gga gac ata atc gtg gcc atc aac ggg gaa agc gcg gag ggc atg      314
Pro Gly Asp Ile Ile Val Ala Ile Asn Gly Glu Ser Ala Glu Gly Met
 45                  50                  55                  60 ctg cat gcc gag gcc cag agc aag atc cgc cag agc ccc tcg ccc ctg      362
Leu His Ala Glu Ala Gln Ser Lys Ile Arg Gln Ser Pro Ser Pro Leu
                 65                  70                  75 cgg ctg cag ctg gac cgg tct cag gct acg tct cca ggg cag acc aat      410
Arg Leu Gln Leu Asp Arg Ser Gln Ala Thr Ser Pro Gly Gln Thr Asn
             80                  85                  90 ggg gac agc tcc ttg gaa gtg ctg gcg act cgc ttc cag ggc tcc gtg      458
Gly Asp Ser Ser Leu Glu Val Leu Ala Thr Arg Phe Gln Gly Ser Val
             95                 100                 105 agg aca tac act gag agt cag tcc tcc tta agg tcc tcc tac tcc agc      506
Arg Thr Tyr Thr Glu Ser Gln Ser Ser Leu Arg Ser Ser Tyr Ser Ser
110                 115                 120 cca acc tcc ctc agc ccg agg gcc ggc agc ccc ttc tca cca cca ccc      554
Pro Thr Ser Leu Ser Pro Arg Ala Gly Ser Pro Phe Ser Pro Pro Pro
125                 130                 135                 140 tct agc agc tcc ctc act gga gag gca gcc atc agc cgc agc ttc cag      602
Ser Ser Ser Ser Leu Thr Gly Glu Ala Ala Ile Ser Arg Ser Phe Gln
                145                 150                 155 agt ctg gca tgt tcc ccg ggc ctc ccc gct gct gac cgc ctg tcc tac      650
Ser Leu Ala Cys Ser Pro Gly Leu Pro Ala Ala Asp Arg Leu Ser Tyr
            160                 165                 170 tca ggc cgc cct gga agc cga cag gcc ggc ctc ggc cgc gct ggc gac      698
Ser Gly Arg Pro Gly Ser Arg Gln Ala Gly Leu Gly Arg Ala Gly Asp
            175                 180                 185 tcg gcg gtg ctg gtg ctg ccg cct tcc ccg ggc cct cgt tcc tcc agg      746
Ser Ala Val Leu Val Leu Pro Pro Ser Pro Gly Pro Arg Ser Ser Arg
        190                 195                 200 ccc agc atg gac tcg gaa ggg gga agc ctc ctg ctg gac gag gac tcg      794
Pro Ser Met Asp Ser Glu Gly Gly Ser Leu Leu Leu Asp Glu Asp Ser
205                 210                 215                 220 gaa gtc ttc aag atg ctg cag gaa aat cgc gag gga cgg gcg gcc ccc      842
Glu Val Phe Lys Met Leu Gln Glu Asn Arg Glu Gly Arg Ala Ala Pro
                225                 230                 235 cga cag tcc agc tcc ttt cgg ctc ttg cag gaa gcc ctg gag gct gag      890
Arg Gln Ser Ser Ser Phe Arg Leu Leu Gln Glu Ala Leu Glu Ala Glu
```

```
                Arg Gln Ser Ser Ser Phe Arg Leu Leu Gln Glu Ala Leu Glu Ala Glu
                                240                 245                 250 gag aga ggt ggc acg cca gcc ttc ttg ccc agc tca ctg agc ccc cag           938
Glu Arg Gly Gly Thr Pro Ala Phe Leu Pro Ser Ser Leu Ser Pro Gln
            255                 260                 265 tcc tcc ctg ccc gcc tcc agg gcc ctg gcc acc cct ccc aag ctc cac           986
Ser Ser Leu Pro Ala Ser Arg Ala Leu Ala Thr Pro Pro Lys Leu His
        270                 275                 280 act tgt gag aag tgc agt acc agc atc gcg aac cag gct gtg cgc atc          1034
Thr Cys Glu Lys Cys Ser Thr Ser Ile Ala Asn Gln Ala Val Arg Ile
285                 290                 295                 300 cag gag ggc cgg tac cgc cac ccc ggc tgc tac acc tgt gcc gac tgt          1082
Gln Glu Gly Arg Tyr Arg His Pro Gly Cys Tyr Thr Cys Ala Asp Cys
                305                 310                 315 ggg ctg aac ctg aag atg cgc ggg cac ttc tgg gag gac gct tgt gct          1130
Gly Leu Asn Leu Lys Met Arg Gly His Phe Trp Glu Asp Ala Cys Ala
            320                 325                 330 atg gag gga atg aga ttg tca ctg gaa gct ttg gag ggg atg gtg gag          1178
Met Glu Gly Met Arg Leu Ser Leu Glu Ala Leu Glu Gly Met Val Glu
        335                 340                 345 ggc gcc aag cgg agg gac agg agg aag acc agg aga ccc atc cag cca          1226
Gly Ala Lys Arg Arg Asp Arg Arg Lys Thr Arg Arg Pro Ile Gln Pro
    350                 355                 360 agc tgg tga gacaacctct gatcctgagg accggccgcc caccaagggt                  1275
Ser Trp
365 tgggcccccg gggccaggtt gatctaccga caccttccac ttctttcctg ggagagactg        1335 ctggcttcat tggtgattga tttggagggg ggaaaaaggg cagggtggct caggctttag        1395 gcccaggtac tggggaggcc tgaggagccc tcctggagct caggaggccg aggctgcctt        1455 gagctgtgat cgtgccactg cattccagcc tgggagagag agaggacctg tctgttgaaa        1515 aaaacacaaa aacaaatgaa tgcatgtggc cagtgccagg tgagctgccc tgggggttca        1575 ctggagttga ggcaggggac agtagtctcc cctgccagcc taggattttg ggcgtcattc        1635 acccactacc cctagtgcta gtcccagagg atgctgcgga gggggcagcc tcagctctct        1695 tttcagagaa gatcaaagct gggcttccca gggtgcctgg ctggtccctg ccggcagctt       1755 tgtgctctcc ggctctttgt gaaaggaatc ttggcgcaga tgtttgtgtt gcctcctcag        1815 gcacctgtag atataattta caccatgata tcattgtctc acctttttgcc tgggtggctg      1875 cctgagaaag gtctttcttt ttatagaaaa gatcaaggct gtctggcgcg ggactccatg       1935 agccccaggc gctggtcaga aacggggtag tctctttggc gccacctagt gtccagtttg        1995 gcccatggcg gggcccattc acggggcaac actgggcttc tggcacagc gggaatacag         2055 aaagatacag cactcctcat gccttcctgg aggtagaagg ccagtggcag cgactgagct       2115 ggcatgaatg aataagagga tgtggcactg agcgccaagg gctaccttgg aacgcaccga       2175 ggagcgtccc gtgagttcaa agcagtggcc gtgatgcaaa aggagggctg ggtcttggag       2235 acgtggagaa gaggaatgct gagtgatggg gtggctgctg gggggatgct tagctcagag        2295 cagtggctga tggggacact gagataagat cggaggggag ctgtcaatgc agaagtggt       2355 ttgaacttcc ccttgaggct ctagggacat tttgttttga gacatggtct tgctctattg        2415 cccaggctgg agtgcagtgg tacagtctta gctcactgca gcctccacct cccaggctca       2475 agagatcctc ccacagcctc ccaggtagct gggactacag gcgtgcacca ccacacccag        2535 ctaattttta agttttttttt ttttttaag agatgggtc tcactatgtt gcccaggctg         2595 gtctcgaact tcgggcccca agccatcctc ccaccttggc tttccaaagt gttgggatta       2655
```

| | |
|---|---|
| caagcgtgag ctaaccttgc ccagcctctg ggaacacttg gaaggtttta agcagagaag | 2715 |
| tgacaggttg gaaagatgg tttggattat tgatatggac agattcccac ctgtatgtag | 2775 |
| cacgccatgc tgggccagca gtgtcatagg agtggagggg gataagtggg gactggggac | 2835 |
| atgtgaaatg atgggcattc cagtgaggca tcgaatgcct tctgagggct ttgtaggttc | 2895 |
| cagctcaaat cccctctgg ctcttgttct ttggtgtggc agccatctct cctcccaggg | 2955 |
| gtcctgaggg tttcagcacc agggttctct gcagccacac aatcagcccg gctcgggagc | 3015 |
| aaactcccct ggaagaacgg agttatgagt tggtcagcag aggaggctgg ggacaggcag | 3075 |
| ttttggtct tttacctctg atcttgtccc caacctaagc cagctagctg cgtgctccca | 3135 |
| ctccctctgc cgcacgccgc ccgtctatgt tcccggactt tgtccagtgc agtgccctct | 3195 |
| tcccttcctg cactgaggag attaactgaa gtgacagatt agagttagaa gtggcccaaa | 3255 |
| ggagcatctg gtacaacccc ctttggttag agaagggaaa gtgacttttc caaagctgca | 3315 |
| cagctagaca gtcataatgg ctaagctctg ggggtgcttt tgatgtgcta gggatacttc | 3375 |
| caatgcttta actcacttaa tcctcacaac ccgagatagg tactgttacc atcctctctg | 3435 |
| cagacgagga aaccgaggac caggaggttc agtaaatggt ccaagtactc ctagctagta | 3495 |
| aggaatggat ctacagcctg cctcccaggt ttctggcttg tggggggcag agtttgtccc | 3555 |
| tctgtcatca gaggcagcct tccaggcaca gctctggtca cctctggtca caactggagg | 3615 |
| tcaccacagc cctccccagc gctctgtagg ctctcagctt tgtgcttcct cccacgggta | 3675 |
| ctagctccag ctgagcttgc aggaaaccca cttcctgaag ccaggacttc cccatgggaa | 3735 |
| gtgcaggggc cactgggcag cctgagggct gaccctgctc aggacactgt ctgtctcagg | 3795 |
| aactcatggc agtggtttac cttgtcagga gtgcatggac gggctgcccc tcccattcct | 3855 |
| tcaagcatca ctcagagagc cctggcctgg ctctaggctt gggactgcgg ctgccacagg | 3915 |
| aaggggcat cccctactt tgggtgttgg gtcagatcct gccccgtgc cgccagggc | 3975 |
| tcaggttcct ctgagctggt cctgggccag gacgcatctg catggcggtg gtggggagga | 4035 |
| ggggtgcgcc atggcctgga ggggagtgtg tgttggggtg tgtgtgtgga ggttctttg | 4095 |
| agtcacacac aaagcattgt gctgagacac tgcattcctg ctggctgggc ttcctgtttc | 4155 |
| cagatgcatt cctgtcccag agtcaccaca gagactgttt ggaatcccgc cccacattct | 4215 |
| ccaaattcag ggcgcgatct ggcaaaggct ccctccccca ccctcttact ttggagggag | 4275 |
| tctgggctcc ctcctaccca ggggagggctg gcagggctct ggcacggccg gggtgtgatt | 4335 |
| ccacacatct tcttggtctt gcataaggca gttcctggag acccagcact ctggttctct | 4395 |
| ctctgcctgt gagaagcgga atgggtactg tctaggagga ctgggcaggg tgggggcaac | 4455 |
| ccagaggacc catggctagc agggaagggc ctgggcttga atgtgactct gttgagacat | 4515 |
| ggccagcaat tctggcactt ggctgtcatt cggctggcct cgcagagat tggctgtggg | 4575 |
| cctcagtttc cccattttat aaagttttaa aatctg | 4611 |

<210> SEQ ID NO 2
<211> LENGTH: 366
<212> TYPE: PRT
<213> ORGANISM: Homo sapiens

<400> SEQUENCE: 2

Met Ala Leu Thr Val Asp Val Ala Gly Pro Ala Pro Trp Gly Phe Arg
1               5                   10                  15

Ile Thr Gly Gly Arg Asp Phe His Thr Pro Ile Met Val Thr Lys Val
            20                  25                  30

```
Ala Glu Arg Gly Lys Ala Lys Asp Ala Asp Leu Arg Pro Gly Asp Ile
        35                  40                  45
Ile Val Ala Ile Asn Gly Glu Ser Ala Glu Gly Met Leu His Ala Glu
 50                  55                  60
Ala Gln Ser Lys Ile Arg Gln Ser Pro Ser Pro Leu Arg Leu Gln Leu
 65                  70                  75                  80
Asp Arg Ser Gln Ala Thr Ser Pro Gly Gln Thr Asn Gly Asp Ser Ser
                 85                  90                  95
Leu Glu Val Leu Ala Thr Arg Phe Gln Gly Ser Val Arg Thr Tyr Thr
            100                 105                 110
Glu Ser Gln Ser Ser Leu Arg Ser Ser Tyr Ser Ser Pro Thr Ser Leu
        115                 120                 125
Ser Pro Arg Ala Gly Ser Pro Phe Ser Pro Pro Ser Ser Ser Ser Ser
    130                 135                 140
Leu Thr Gly Glu Ala Ala Ile Ser Arg Ser Phe Gln Ser Leu Ala Cys
145                 150                 155                 160
Ser Pro Gly Leu Pro Ala Ala Asp Arg Leu Ser Tyr Ser Gly Arg Pro
                165                 170                 175
Gly Ser Arg Gln Ala Gly Leu Gly Arg Ala Gly Asp Ser Ala Val Leu
            180                 185                 190
Val Leu Pro Pro Ser Pro Gly Pro Arg Ser Ser Arg Pro Ser Met Asp
        195                 200                 205
Ser Glu Gly Gly Ser Leu Leu Leu Asp Glu Asp Ser Glu Val Phe Lys
    210                 215                 220
Met Leu Gln Glu Asn Arg Glu Gly Arg Ala Ala Pro Arg Gln Ser Ser
225                 230                 235                 240
Ser Phe Arg Leu Leu Gln Glu Ala Leu Glu Ala Glu Arg Gly Gly
                245                 250                 255
Thr Pro Ala Phe Leu Pro Ser Ser Leu Ser Pro Gln Ser Ser Leu Pro
            260                 265                 270
Ala Ser Arg Ala Leu Ala Thr Pro Pro Lys Leu His Thr Cys Glu Lys
        275                 280                 285
Cys Ser Thr Ser Ile Ala Asn Gln Ala Val Arg Ile Gln Glu Gly Arg
    290                 295                 300
Tyr Arg His Pro Gly Cys Tyr Thr Cys Ala Asp Cys Gly Leu Asn Leu
305                 310                 315                 320
Lys Met Arg Gly His Phe Trp Glu Asp Ala Cys Ala Met Glu Gly Met
                325                 330                 335
Arg Leu Ser Leu Glu Ala Leu Glu Gly Met Val Glu Gly Ala Lys Arg
            340                 345                 350
Arg Asp Arg Arg Lys Thr Arg Arg Pro Ile Gln Pro Ser Trp
        355                 360                 365

<210> SEQ ID NO 3
<211> LENGTH: 1550
<212> TYPE: DNA
<213> ORGANISM: Mus musculus
<220> FEATURE:
<221> NAME/KEY: CDS
<222> LOCATION: (67)..(1116)

<400> SEQUENCE: 3
gagcaactga agaggcagga ggcagctgcg tgggctctca actccccagg gcaagagttg      60 ccaggc atg gcg ttg act gtg gat gtg gca gga cca gca cct tgg ggc       108
       Met Ala Leu Thr Val Asp Val Ala Gly Pro Ala Pro Trp Gly
         1               5                  10
```

-continued

| | | |
|---|---|---|
| ttc cga att agc ggg ggc aga gat ttc cac aca ccc atc att gtg acc<br>Phe Arg Ile Ser Gly Gly Arg Asp Phe His Thr Pro Ile Ile Val Thr<br>15                    20                    25                    30 | | 156 |
| aag gtc aca gag cgg ggc aag gct gaa gca gct gat ctc cgg cct ggc<br>Lys Val Thr Glu Arg Gly Lys Ala Glu Ala Ala Asp Leu Arg Pro Gly<br>                  35                    40                    45 | | 204 |
| gac atc att gtg gcc atc aat gga cag agt gca gag aac atg cta cac<br>Asp Ile Ile Val Ala Ile Asn Gly Gln Ser Ala Glu Asn Met Leu His<br>                50                    55                    60 | | 252 |
| gcg gag gcc caa agc aag atc cga cag agc gcc tca ccc cta aga ctg<br>Ala Glu Ala Gln Ser Lys Ile Arg Gln Ser Ala Ser Pro Leu Arg Leu<br>65                    70                    75 | | 300 |
| cag ctg gac cgg tcc caa aca gcc tct cct ggg cag acc aat ggg gag<br>Gln Leu Asp Arg Ser Gln Thr Ala Ser Pro Gly Gln Thr Asn Gly Glu<br>      80                    85                    90 | | 348 |
| ggc tcc ttg gaa gtg ctg gca acc aga ttc cag ggc tcc ctg agg aca<br>Gly Ser Leu Glu Val Leu Ala Thr Arg Phe Gln Gly Ser Leu Arg Thr<br>95                    100                 105            110 | | 396 |
| cac cgt gac agc cag tct tcc cag agg tct gcc tgc ttc agc cca gtc<br>His Arg Asp Ser Gln Ser Ser Gln Arg Ser Ala Cys Phe Ser Pro Val<br>                 115                    120                 125 | | 444 |
| tct ctc agc ccc agg cct tgc agc ccc ttc tcc acc cca ccc cct acc<br>Ser Leu Ser Pro Arg Pro Cys Ser Pro Phe Ser Thr Pro Pro Pro Thr<br>          130                 135                 140 | | 492 |
| agc cca gtt gcc ctt tct aaa gag gat atg att ggc tgt agt ttc cag<br>Ser Pro Val Ala Leu Ser Lys Glu Asp Met Ile Gly Cys Ser Phe Gln<br>               145                 150                 155 | | 540 |
| agt ctg aca cac tct cca ggc ctt gct gct gct cac cac ttg acc tac<br>Ser Leu Thr His Ser Pro Gly Leu Ala Ala Ala His His Leu Thr Tyr<br>        160                 165                 170 | | 588 |
| cct ggc cac ccc acc agc caa cag gcc ggc cac agc agc cca agc gac<br>Pro Gly His Pro Thr Ser Gln Gln Ala Gly His Ser Ser Pro Ser Asp<br>175                    180                 185                 190 | | 636 |
| tcc gca gtg agg gtg ctg ctc cat tcc cca gga cgg ccc tcc agc cct<br>Ser Ala Val Arg Val Leu Leu His Ser Pro Gly Arg Pro Ser Ser Pro<br>               195                 200                 205 | | 684 |
| agg ttc agc agt ttg gat ctg gag gaa gac tca gag gtg ttc aag atg<br>Arg Phe Ser Ser Leu Asp Leu Glu Glu Asp Ser Glu Val Phe Lys Met<br>          210                 215                 220 | | 732 |
| ctg cag gag aac cgc cag gga cgg gcc gcc cca agg cag tcc agc tct<br>Leu Gln Glu Asn Arg Gln Gly Arg Ala Ala Pro Arg Gln Ser Ser Ser<br>               225                 230                 235 | | 780 |
| ttt cga ctc tta cag gaa gcc ttg gag gct gag gag aga ggt ggc aca<br>Phe Arg Leu Leu Gln Glu Ala Leu Glu Ala Glu Glu Arg Gly Gly Thr<br>240                    245                 250 | | 828 |
| cct gcc ttt gtg ccc agc tcg ctg agc tcc cag gct tcc ttg ccc acc<br>Pro Ala Phe Val Pro Ser Ser Leu Ser Ser Gln Ala Ser Leu Pro Thr<br>255                    260                 265                 270 | | 876 |
| tcc agg gcc ttg gcc act cca ccc aag ctc cac acc tgt gag aaa tgc<br>Ser Arg Ala Leu Ala Thr Pro Pro Lys Leu His Thr Cys Glu Lys Cys<br>               275                 280                 285 | | 924 |
| agc gtc aac atc tcg aac cag gcg gtc cgc atc cag gag ggg agg tac<br>Ser Val Asn Ile Ser Asn Gln Ala Val Arg Ile Gln Glu Gly Arg Tyr<br>          290                 295                 300 | | 972 |
| cga cac cct ggc tgc tac act tgc gca gac tgt ggg ctg aac ctg aag<br>Arg His Pro Gly Cys Tyr Thr Cys Ala Asp Cys Gly Leu Asn Leu Lys<br>        305                 310                 315 | | 1020 |
| atg cgc ggc cac ttc tgg gtg ggc aat gag ttg tac tgc gag aag cat<br>Met Arg Gly His Phe Trp Val Gly Asn Glu Leu Tyr Cys Glu Lys His<br>320                    325                 330 | | 1068 |

```
gcc cgc cag cgc tac tct atg cct gga act ctc aac tct cga gcc tga    1116
Ala Arg Gln Arg Tyr Ser Met Pro Gly Thr Leu Asn Ser Arg Ala
335                 340                 345 gcctcaaggt gctcggcctg tctgcactct cagactctgc agacatgatt atactgagag    1176
caagcaggga agqggtgata gcaggtgata gatgatctta catgaactaa ggttggggag    1236 tccccttttgt ccttgctggg tgaggccaag ggttgggact aatgtcaggt tgctagtgct    1296
aaggacagtt ccactctctc tggccttcct cctgcaggcc aggttctgta ttacggtcta    1356
cagtggctgc catgtttgac acgaaagcgt atggggttgg gcatggatag aagcatctag    1416
aagggaatgg tgggcctgag gtaaatgata ttcatggtgt gaagtttcta acatatgaac    1476
tctatataca cgtggataaa attaagtagt gtattttcaa aaaaaaaaa aaaaaaaaa     1536 aaaaaaaaaa aaaa                                                     1550

<210> SEQ ID NO 4
<211> LENGTH: 349
<212> TYPE: PRT
<213> ORGANISM: Mus musculus

<400> SEQUENCE: 4

Met Ala Leu Thr Val Asp Val Ala Gly Pro Ala Pro Trp Gly Phe Arg
1               5                   10                  15

Ile Ser Gly Gly Arg Asp Phe His Thr Pro Ile Ile Val Thr Lys Val
                20                  25                  30

Thr Glu Arg Gly Lys Ala Glu Ala Ala Asp Leu Arg Pro Gly Asp Ile
            35                  40                  45

Ile Val Ala Ile Asn Gly Gln Ser Ala Glu Asn Met Leu His Ala Glu
        50                  55                  60

Ala Gln Ser Lys Ile Arg Gln Ser Ala Ser Pro Leu Arg Leu Gln Leu
65                  70                  75                  80

Asp Arg Ser Gln Thr Ala Ser Pro Gly Gln Thr Asn Gly Glu Gly Ser
                85                  90                  95

Leu Glu Val Leu Ala Thr Arg Phe Gln Gly Ser Leu Arg Thr His Arg
            100                 105                 110

Asp Ser Gln Ser Ser Gln Arg Ser Ala Cys Phe Ser Pro Val Ser Leu
        115                 120                 125

Ser Pro Arg Pro Cys Ser Pro Phe Ser Thr Pro Pro Pro Thr Ser Pro
130                 135                 140

Val Ala Leu Ser Lys Glu Asp Met Ile Gly Cys Ser Phe Gln Ser Leu
145                 150                 155                 160

Thr His Ser Pro Gly Leu Ala Ala Ala His His Leu Thr Tyr Pro Gly
                165                 170                 175

His Pro Thr Ser Gln Gln Ala Gly His Ser Ser Pro Ser Asp Ser Ala
            180                 185                 190

Val Arg Val Leu Leu His Ser Pro Gly Arg Pro Ser Ser Pro Arg Phe
        195                 200                 205

Ser Ser Leu Asp Leu Glu Glu Asp Ser Glu Val Phe Lys Met Leu Gln
210                 215                 220

Glu Asn Arg Gln Gly Arg Ala Ala Pro Arg Gln Ser Ser Ser Phe Arg
225                 230                 235                 240

Leu Leu Gln Glu Ala Leu Glu Ala Glu Arg Gly Gly Thr Pro Ala
                245                 250                 255

Phe Val Pro Ser Ser Leu Ser Ser Gln Ala Ser Leu Pro Thr Ser Arg
            260                 265                 270
```

```
Ala Leu Ala Thr Pro Pro Lys Leu His Thr Cys Glu Lys Cys Ser Val
        275                 280                 285

Asn Ile Ser Asn Gln Ala Val Arg Ile Gln Glu Gly Arg Tyr Arg His
        290                 295                 300

Pro Gly Cys Tyr Thr Cys Ala Asp Cys Gly Leu Asn Leu Lys Met Arg
305                 310                 315                 320

Gly His Phe Trp Val Gly Asn Glu Leu Tyr Cys Glu Lys His Ala Arg
                325                 330                 335

Gln Arg Tyr Ser Met Pro Gly Thr Leu Asn Ser Arg Ala
            340                 345

<210> SEQ ID NO 5
<211> LENGTH: 25
<212> TYPE: DNA
<213> ORGANISM: Mus musculus

<400> SEQUENCE: 5
cagagatttc cacacaccca tcatt                                          25

<210> SEQ ID NO 6
<211> LENGTH: 25
<212> TYPE: DNA
<213> ORGANISM: Mus musculus

<400> SEQUENCE: 6
cagtttacac ccacataccc gaatt                                          25

<210> SEQ ID NO 7
<211> LENGTH: 25
<212> TYPE: DNA
<213> ORGANISM: Homo sapiens

<400> SEQUENCE: 7
tgatggccac gattatgtct ccagg                                          25

<210> SEQ ID NO 8
<211> LENGTH: 25
<212> TYPE: DNA
<213> ORGANISM: Mus musculus

<400> SEQUENCE: 8
cacacctgtg agaaatgcag cgtca                                          25
```

US 7,960,363 B2

THERAPEUTIC AGENT FOR WOUNDS AND SCREENING METHOD FOR THE SAME

CROSS-REFERENCE TO THE RELATED APPLICATION

This application is based on a patent application No. 2009-112250 filed in Japan (filing date: May 1, 2009), the contents of which are incorporated in full herein by this reference.

TECHNICAL FIELD OF THE INVENTION

The present invention relates to a therapeutic agent for wounds and a screening method for the same.

BACKGROUND ART OF THE INVENTION

Wound healing is a series of reactions that repair the defects of epithelial tissues in the skin and the like, being one of the most organized immune or inflammatory reactions. A wound healing reaction proceeds in three stages: (1) inflammation stage (2) granulation stage, and (3) remodeling stage. In the inflammation stage, an inflammatory reaction is induced locally upon tissue damage, and neutrophils and macrophages migrate to the wounded site. Macrophages secrete various inflammatory cytokines and chemokines to enhance the inflammatory reaction. In the following granulation stage, angiogenesis is induced by proliferation of vascular endothelial cells, and at the same time fibroblasts infiltrating the wounded site proliferate and produce extracellular matrix such as collagen to form granulation tissue for tissue regeneration. Furthermore, fibroblasts in the granulation tissue differentiate into myofibroblasts, which are rich in actin and highly contractile. The wound contraction, which is mainly mediated by the myofibroblasts, is a useful tool for efficiently reducing wound areas. In the remodeling stage, epithelial cell formation is induced on the granulation tissue, where the original normal structure is remodeled. Impaired wound healing reaction, accompanied with systemic or local pathological conditions, leads to treatment-resistant wounds such as bedsores, postoperative infections at wounded sites, diabetic ulcers, and burns. On the other hand, execessive wound healing reaction causes various fibrotic disorders, for example, keloidosis and scar in the skin, and airway remodeling in asthma in the lungs. In severer cases, the exaggerated wound healing may cause scleroderma, pulmonary fibrosis, liver cirrhosis and the like. For this reason, this series of wound healing reactions must be strictly controlled. Although cytokines such as TGFβ and IL-6, and growth factors such as PDGF and FGF, are reported to play important roles in the progression of wound healing reactions, it remains unclear how these reactions are regulated.

PDLIM2 (PDZ and LIM domain protein-2), also known as SLIM (STAT-interacting LIM protein), is a nuclear ubiquitin ligase, which was isolated by the present inventors. PDLIM2 has both PDZ and LIM domains and belongs to LIM protein family. PDLIM2 binds to STAT4, a transcription factor essential to Th1 cell differentiation in T cells, in the nucleus, and terminates STAT4-mediated signal transduction by ubiquitinating and degrading STAT4 protein (Non-patent Document 1, Patent Document 1). Later analysis revealed that PDLIM2 is a nuclear ubiquitin ligase for NF-κB, terminating inflammatory responses by ubiquitinating, degrading and inactivating NF-κB in dendritic cells (Non-patent Document 2, Patent Document 2). PDLIM2 deficiency in dendritic cells results in defective NF-κB degradation and the production of two- to three-fold more proinflammatory cytokines. However, in vivo functions of PDLIM2 remain unclear so far.

[Patent Document 1] Specification for US-B-application No. 2006/246543
[Patent Document 2] JP-A-2007-254465
[Non-patent Document 1] Tanaka et al., Immunity, 22, 729-736, 2005
[Non-patent Document 2] Tanaka et al., Nat. Immunol. 8, 584, 2007

SUMMARY OF THE INVENTION

It is an object of the present invention to elucidate the role of PDLIM2 in wound healing reactions and apply the findings to drug discovery.

The present inventors performed a study of wound healing using PDLIM2-deficient mice. As a result, wound healing was promoted in the PDLIM2-deficient mice than in wild type mice. In vitro analysis revealed that PDLIM2, as a nuclear ubiquitin ligase for Smad2 and Smad3, negatively regulates the TGFβ-mediated Smad activation by ubiquitinating and degrading these transcription factors. Differentiation into myofibroblasts induced by TGFβ was augmented in PDLIM2-deficient fibroblasts. Furthermore, differentiation into myofibroblasts induced by TGFβ was enhanced by a specific siRNA against PDLIM2. These results suggested that in wound healing reactions, PDLIM2 might play a role in terminating wound healing reactions at an appropriate time so as to prevent the wound healing reactions from occurring in excess by negatively regulating the TGFβ-dependent signal transduction pathway. When an siRNA against PDLIM2 was administered to wound model mice, wound healing reactions were promoted.

Based on these findings, the present invention has been developed.

Accordingly, the present invention relates to the following:

[1] A therapeutic method for wounds in a mammal, comprising administering an effective amount of a substance that suppresses the expression or function of PDLIM2 to the mammal.

[2] The method according to [1], wherein the substance that suppresses the expression or function of PDLIM2 is an siRNA or antisense nucleic acid capable of specifically suppressing the expression of PDLIM2, or an expression vector capable of expressing said polynucleotide.

[3] A screening method for a substance capable of treating wounds, comprising determining whether or not a test substance is capable of suppressing the expression or function of PDLIM2.

[4] The screening method according to [3], wherein screening is performed by a step selected from the group consisting of 1) a measurement of the expression of PDLIM2 using cells permitting a measurement of the expression of PDLIM2, 2) a measurement of a function of PDLIM2 using a reconstructed system permitting a measurement of the function of PDLIM2, 3) a measurement of a function of PDLIM2 using a cell system enabling a measurement of a function of PDLIM2, and 4) a measurement of the expression or function of PDLIM2 using an animal.

[5] The screening method according to [3], wherein the determination is performed on the basis of a determination of whether or not the test substance is capable of suppressing the ubiquitination of Smad2 or Smad3 by PDLIM2.

[6] The screening method according to [3], wherein the determination is performed on the basis of a determination of whether or not the test substance is capable of suppressing the formation of a complex containing PDLIM2 and Smad2 or Smad3.

[7] A complex containing PDLIM2 and Smad2 or Smad3.

[8] A therapeutic agent for wounds containing a substance that suppresses the expression or function of PDLIM2.

[9] The therapeutic agent according to [8], wherein the substance that suppresses the expression or function of PDLIM2 is an siRNA or antisense nucleic acid capable of specifically suppressing the expression of PDLIM2, or an expression vector capable of expressing said polynucleotide.

ADVANTAGES

The present invention provides a therapeutic agent for wounds based on a new mechanism that has not been known to date, i.e., suppression of the expression or function of PDLIM2, and a screening method for the same.

Figure 1:
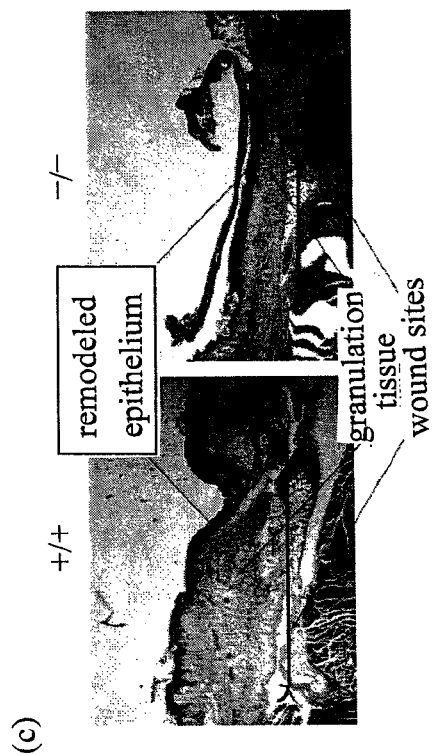
FIG. 1 shows wound contraction promoted in PDLIM2-deficient mice. (a) Wound healing in wild type mice (+/+) and PDLIM2-deficient mice (−/−) as of 7 days after wounding; representative results from three independent experiments using five animals per group are shown. (b) Time-related changes in the area of wound site compared with the initial area of wound site. (c) Histological examination of wild type mice and PDLIM2-deficient mice as of 7 days after wounding; H-E staining, original magnification rate=×10. (d) Contraction of type I collagen gel mediated by wild-type fibroblasts or PDLIM2-deficient fibroblasts; the cells were embedded in collagen gel, the gel was floated, and the cells were cultured with or without addition of TGFβ; gel surface areas were measured 0, 8 and 24 hours after release of the gel.
Figure 1:
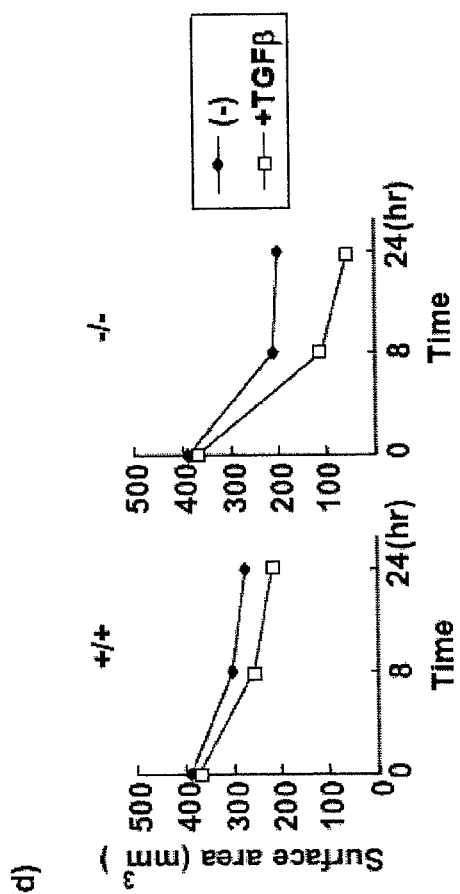
Figure 1:
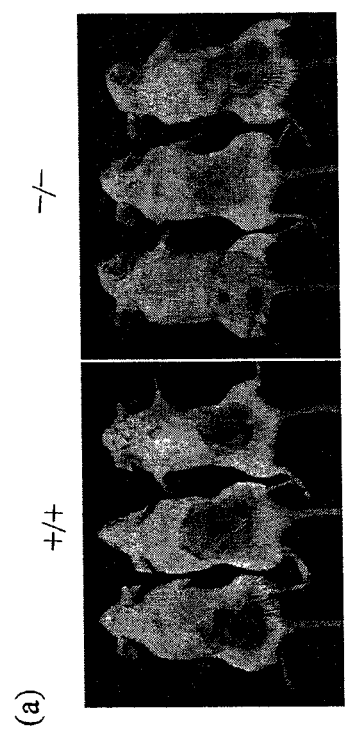
Figure 1:
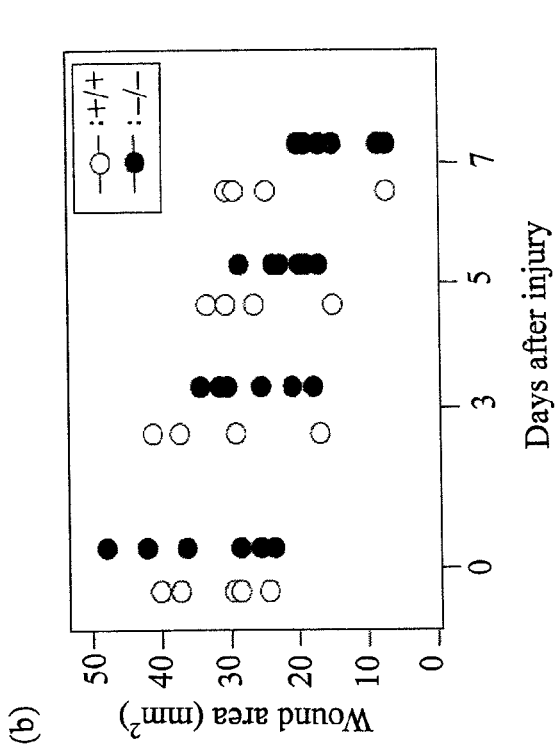

BEST MODE FOR CARRYING OUT THE INVENTION (1. Therapeutic Agent for Wounds)

The present invention provides a therapeutic agent for wounds comprising a substance that suppresses the expression or function of PDLIM2.

PDLIM2 (PDZ and LIM domain protein-2), also known as SLIM (STAT-interacting LIM protein), is a publicly known intranuclear ubiquitin ligase belonging to the LIM protein family, having PDZ and LIM domains (Non-patent Document 1).

As mentioned herein, PDLIM2 is generally derived from a warm-blooded animal (mammal or bird). Examples of the mammal include, but are not limited to, laboratory animals such as mice, rats, hamsters, guinea pigs, and other rodents, and rabbits; domestic animals such as swines, bovines, goat, horses, sheep, and minks; companion animals such as dogs and cats; and primates such as humans, monkeys, cynomolgus monkeys, rhesus monkeys, marmosets, orangutans, and chimpanzees. Examples of the bird include chicken, quails, domestic ducks, geese, turkeys, emus, ostriches, guinea fowls, pigeons and the like. PDLIM2 is preferably derived from a mammal, more preferably from a primate (human etc.) or a rodent (mouse etc.).

"PDLIM2 is derived from a mammal" means that a sequence (nucleotide sequence or amino acid sequence) of PDLIM2 is of mammalian origin.

Nucleotide sequences and amino acid sequences of PDLIM2 are known in the public. Representative nucleotide sequences and amino acid sequences of human and mouse PDLIM2 are registered with NCBI as follows:
[Human PDLIM2]
Nucleotide sequence (cDNA sequence): accession number NM_176871 (version NM_176871.2) (SEQ ID NO: 1)
Amino acid sequence: accession number NP 789847 (NP_789847.1) (SEQ ID NO: 2)
[Mouse PDLIM2]
Nucleotide sequence (cDNA sequence): accession number NM_145978 (version NM_145978.1) (SEQ ID NO: 3)
Amino acid sequence: accession number NP_666090 (version NP_666090.1) (SEQ ID NO: 4)

Nucleotide sequences are herein described as DNA sequences unless otherwise specified; however, when the polynucleotide is an RNA, thymine (T) should read as uracil (U) as appropriate.

Functions of PDLIM2 include binding with Smad2 or Smad3, ubiquitination of Smad2 or Smad3 and the like.

Examples of the substance that suppresses the expression or function of PDLIM2 include an siRNA or antisense nucleic acid capable of specifically suppressing the expression of PDLIM2, an expression vector capable of expressing said polynucleotide, and low molecular compounds. Preferably, an siRNA or antisense nucleic acid capable of specifically suppressing the expression of PDLIM2, or an expression vector capable of expressing said polynucleotide is used.

As mentioned herein, "specific suppression of gene expression" means that the expression of the targeted gene is more strongly suppressed than the expression of other genes.

Examples of the siRNA capable of specifically suppressing the expression of PDLIM2 include:
(A) a double-stranded RNA comprising a nucleotide sequence complementary to the nucleotide sequence of an mRNA (mature mRNA or initial transcription product) that encodes PDLIM2 or a partial sequence thereof having 18 bases or more in length, and
(B) a double-stranded RNA comprising a nucleotide sequence having 18 bases or more in length that is hybridizable specifically with an mRNA (mature mRNA or initial transcription product) that encodes PDLIM2 in cells of an animal (preferably human) which is the subject of treatment, and suppressing the transcription of PDLIM2 by hybridizing therewith.

As mentioned herein, "specific hybridization" means that a nucleic acid hybridizes more strongly with a targeted nucleotide than with other nucleotides.

Examples of the nucleotide sequence of an mRNA that encodes PDLIM2 include the nucleotide sequence shown by SEQ ID NO:1 (human PDLIM2) and the nucleotide sequence shown by SEQ ID NO:3 (mouse PDLIM2).

Transferring a short double-stranded RNA to a cell results in the degradation of mRNAs that are complementary to the RNA. This phenomenon, known as RNA interference (RNAi), has long been known to occur in nematodes, insects, plants and the like. Recently, this phenomenon was confirmed as occurring also in animal cells [Nature, 411(6836): 494-498 (2001)], and this is attracting attention as a substitute technique for ribozyme.

A representative siRNA is a double-stranded oligo-RNA consisting of an RNA having a nucleotide sequence complementary to the nucleotide sequence of the mRNA of the target gene or a partial sequence thereof (hereinafter, target nucleotide sequence) and a complementary strand for the same. A single-stranded RNA wherein a sequence complementary to the target nucleotide sequence (first sequence) and a complementary sequence for the same (second sequence) are joined together via a hairpin loop portion, and wherein the first sequence forms a double-stranded structure with the second sequence by assuming a hairpin loop form structure (small hairpin RNA: shRNA), also represents a preferred embodiment of siRNA.

The length of the portion complementary to the target nucleotide sequence, contained in the siRNA, is generally about 18 bases or more, preferably 19 bases or more, more preferably about 21 bases or more, but is not limited, as far as the expression of the target gene can specifically be suppressed. If the siRNA is longer than 23 bases, the siRNA may undergo degradation in cells to produce an siRNA having about 20 bases in length; therefore, theoretically, the upper limit of the portion complementary to the target nucleotide sequence is the full length of the nucleotide sequence of an mRNA (mature mRNA or initial transcription product) of the target gene. Taking into account the avoidance of interferon induction, the ease of synthesis, antigenicity issues and the like, however, the length of the complementary portion is, for example, about 50 bases or less, preferably about 25 bases or less, most preferably about 23 bases or less. Hence, the length of the complementary portion is generally about 18 to 50 bases, preferably about 19 to about 25 bases, more preferably about 21 to about 23 bases.

The length of each RNA strand that constitutes the siRNA is generally about 18 bases or more, preferably 19 bases or more, more preferably about 21 bases or more, but is not limited, as far as the expression of the target gene can specifically be suppressed; there is theoretically no upper limit on the length of each RNA strand. Taking into account the avoidance of interferon induction, the ease of synthesis, antigenicity issues and the like, however, the length of the siRNA is, for example, about 50 bases or less, preferably about 25 bases or less, most preferably about 23 bases or less. Hence, the length of each RNA strand is, for example, generally about 18 to 50 bases, preferably about 19 to about 25 bases, more preferably about 21 to about 23 bases. The length of the shRNA is expressed as the length of the double-stranded moiety when the shRNA assumes a double-stranded structure.

It is preferable that the target nucleotide sequence and the sequence complementary thereto contained in the siRNA be completely complementary to each other. However, in the presence of a base mutation at a position apart from the center of the siRNA (can be fall in the range of identity of at least 90% or more, preferably 95% or more), the cleavage activity by RNA interference is not completely lost, but a partial activity can remain. On the other hand, a base mutation in the center of the siRNA has a major influence to the extent that can extremely reduce the mRNA cleavage activity by RNA interference.

The siRNA may have an additional base that does not form a base pair at the 5'- and/or 3'-terminal. The length of the additional base is not particularly limited, as far as the siRNA can specifically suppress the expression of the target gene; the length is generally 5 bases or less, for example, 2 to 4 bases.

Although the additional base may be a DNA or an RNA, use of a DNA improves the stability of the siRNA. Examples of the sequences of such additional bases include, but are not limited to, the sequences ug-3', uu-3', tg-3', tt-3', ggg-3', guuu-3', gttt-3', ttttt-3', uuuuu-3' and the like.

The length of the loop portion of the hairpin loop of the shRNA is not particularly limited, as far as the expression of the target gene can specifically be suppressed; the length is generally about 5 to 25 bases. The nucleotide sequence of the loop portion is not particularly limited, as far as a loop can be formed, and the shRNA can specifically suppress the expression of the target gene.

"An antisense nucleic acid" refers to a nucleic acid comprising a nucleotide sequence hybridizable specifically with a target mRNA (mature mRNA or initial transcription product) under physiological conditions for the cells that express the target mRNA, and being capable of inhibiting the translation of the polypeptide encoded by the target mRNA in a hybridized state. The choice of antisense nucleic acid may be a DNA or an RNA, or a DNA/RNA chimera, and is preferably a DNA.

Examples of the antisense nucleic acid capable of specifically suppressing the expression of PDLIM2 include:

(A) a nucleic acid comprising a nucleotide sequence complementary to the nucleotide sequence of an mRNA (mature mRNA or initial transcription product) that encodes PDLIM2 or a partial sequence thereof having 12 bases or more in length, (B) a nucleic acid comprising a nucleotide sequence having 12 bases or more in length that is hybridizable specifically with an mRNA (mature mRNA or initial transcription product) that encodes PDLIM2 in cells of an animal (preferably human) which is a the subject of treatment, and being capable of inhibiting the translation into the PDLIM2 polypeptide in a hybridized state, and the like.

The length of the portion that hybridizes with the target mRNA in the antisense nucleic acid is not particularly limited, as far as the expression of PDLIM2 can specifically be suppressed; the length is generally about 12 bases or more, and up to the same length as the full-length sequence of the mRNA (mature mRNA or initial transcription product). Taking into account hybridization specificity, the length is preferably about 15 bases or more, more preferably 18 bases or more. Taking into account the ease of synthesis, antigenicity issues and the like, the length of the portion that hybridizes with the target mRNA is generally about 200 bases or less, preferably about 50 bases or less, more preferably about 30 bases or less. Hence, the length of the portion that hybridizes with the target mRNA is, for example, about 12 to about 200 bases, preferably about 15 to about 50 bases, more preferably about 18 to about 30 bases.

The target nucleotide sequence for the antisense nucleic acid is not particularly limited, as far as the expression of PDLIM2 can specifically be suppressed; the sequence may be the full-length sequence of an mRNA (mature mRNA or initial transcription product) of PDLIM2 or a partial sequence thereof (e.g., about 12 bases or more, preferably about 15 bases or more, more preferably about 18 bases or more), or an intron portion of the initial transcription product; however, preferably, the target sequence is located between the 5'-terminal of the mRNA of PDLIM2 and the C-terminal of the coding region.

The nucleotide sequence of the portion that hybridizes with the target mRNA in the antisense nucleic acid varies depending on the base composition of the target sequence, and has an identity of generally about 90% or more (preferably 95% or more, most preferably 100%) to the complementary sequence for the target sequence so as to be capable of hybridizing with the mRNA of PDLIM2 under physiological conditions.

The size of the antisense nucleic acid is generally about 12 bases or more, preferably about 15 bases or more, more preferably about 18 bases or more. In view of the ease of synthesis, antigenicity issues and the like, the size is generally about 200 bases or less, preferably about 50 bases or less, more preferably about 30 bases or less.

Furthermore, the antisense nucleic acid may be one not only capable of hybridizing with the mRNA or initial transcription product of PDLIM2 to inhibit the translation, but also capable of binding to the PDLIM2 gene, which is a double-stranded DNA, to form a triplex and inhibit the transcription into mRNA.

Because natural nucleic acids have the phosphodiester bond thereof decomposed readily by nucleases being present in the cells, the siRNA and antisense nucleic acid used in the present invention can also be synthesized using a modified nucleotide such as the thiophosphate form (phosphate bond P=O replaced with P=S) or the 2'-O-methyl form, which are stable to nucleases. Other factors important for the design of the siRNA or antisense nucleic acid include increasing the water solubility and cell membrane permeability and the like; these can also be achieved by improving dosage forms, such as the use of liposomes or microspheres.

An siRNA and antisense nucleic acid capable of specifically suppressing the expression of PDLIM2 can be prepared by determining the target sequence on the basis of an mRNA sequence (e.g., nucleotide sequence shown by SEQ ID NO:1 or 3) or chromosomal DNA sequence of PDLIM2, and synthesizing a nucleotide sequence complementary thereto using a commercially available automated DNA/RNA synthesizer (Applied Biosystems, Beckman and the like). The siRNA can be prepared by separately synthesizing a sense strand and an antisense strand using an automated DNA/RNA synthesizer, and denaturing the strands in an appropriate annealing buffer solution at about 90° C. to about 95° C. for about 1 minute, and then performing annealing at about 30° C. to 70° C. for about 1 to about 8 hours. A longer double-stranded polynucleotide can be prepared by synthesizing complementary oligonucleotide strands in a way such that they overlap with each other, annealing the strands, and then performing ligation with a ligase.

A therapeutic agent for wounds of the present invention can also have an expression vector capable of expressing (encoding) an siRNA or antisense nucleic acid that specifically suppresses the expression of PDLIM2 as an active ingredient thereof. In the expression vector, the above-described siRNA or antisense nucleic acid or a nucleic acid (preferably DNA) that encodes the same has been operably linked to a promoter capable of exhibiting promoter activity in cells (e.g., sarcoma cells) of a mammal (preferably human) which is the subject of administration.

Any promoter capable of functioning in the cells of the mammal which is the subject of administration can be used. Useful promoters include pol I promoters, pol II promoters, pol III promoters and the like. Specifically, viral promoters such as the SV40-derived initial promoter and cytomegalovirus LTR, mammalian constitutive protein gene promoters such as the β-actin gene promoter, RNA promoters such as the tRNA promoter, and the like are used.

When the expression of an siRNA is intended, it is preferable that a pol III promoter be used as the promoter. Examples of the pol III promoter include the U6 promoter, H1 promoter, tRNA promoter and the like.

The above-described expression vector preferably contains a transcription termination signal, i.e., a terminator region, downstream of the above-described polynucleotide or nucleic acid that encodes the same. Furthermore, a selection marker gene for selection of transformed cells (e.g., genes that confer resistance to drugs such as tetracycline, ampicillin, and kanamycin, genes that compensate for auxotrophic mutations, and the like) can further be contained.

Although there is no limitation on the choice of expression vector used in the present invention, suitable vectors for administration to mammals such as humans include viral vectors such as retrovirus, adenovirus, and adeno-associated virus. Adenovirus, in particular, has advantages such as very high gene transfer efficiency and transferability to non-dividing cells. Because the integration of transgenes into host chromosome is extremely rare, however, the gene expression is transient and generally persists only for about 4 weeks. Considering the persistence of therapeutic effect, it is also preferable to use adeno-associated virus, which offers a relatively high efficiency of gene transfer, which can be transferred to non-dividing cells as well, and which can be integrated into chromosomes via an inverted terminal repeat (ITR).

A therapeutic agent for wounds of the present invention can contain, in addition to a substance that suppresses the expression or function of PDLIM2, an optionally chosen carrier, for example, a pharmaceutically acceptable carrier.

Examples of the pharmaceutically acceptable carrier include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrants such as starch, carboxymethylcellulose, hydroxypropylstarch, sodium-glycolstarch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and white kerosene; and the like.

When the substance that suppresses the expression or function of PDLIM2 is an siRNA or antisense nucleic acid capable of specifically suppressing the expression of PDLIM2, or an expression vector capable of expressing said polynucleotide, a therapeutic agent for wounds of the present invention may further contain a reagent for nucleic acid transfer in order to promote the transfer of the nucleic acid into a cell. Useful nucleic acid transfer reagents include cationic lipids such as lipofectin, lipofectamine, lipofectamine RNAiMAX, invivofectamine, DOGS (transfectam), DOPE, DOTAP, DDAB, DHDEAB, HDEAB, polybrene, and poly(ethylenimine) (PEI). When a retrovirus is used as the expression vector, retronectin, fibronectin, polybrene and the like can be used as transfer reagents.

Examples of the dosage form for a therapeutic agent for wounds of the present invention include liquids, tablets, pills, drinkable liquids, powders, suspensions, emulsions, granules, extracts, fine granules, syrups, infusions, decoctions, eye drops, troches, poultices, liniments, lotions, eye ointments, plasters, capsules, suppositories, enemas, injections (solutions, suspensions and the like), patches, ointments, jellies, pastes, inhalants, creams, sprays, nasal drops, aerosols and the like.

The content of a substance that suppresses the expression or function of PDLIM2 in the pharmaceutical composition is chosen as appropriate over a wide range without limitations; for example, the content is about 0.01 to 100% by weight of the entire pharmaceutical composition.

A therapeutic agent for wounds of the present invention is administered by a method suitable for each dosage form. Examples of useful methods of administration include direct spraying, application or coating on a specified site on the skin, mucosa or the like for external preparations; oral administration for tablets, pills, drinkable liquids, suspensions, emulsions, granules and capsules; intravenous, intramuscular, intradermal, subcutaneous, intra-articular or intraperitoneal injection for injections; and rectal injection for suppositories.

Although the dosage of an agent of the present invention varies depending on the choice or activity of the active ingredient, dosing route (e.g., oral, non-oral), seriousness of illness, recipient animal species, the recipient's drug tolerance, body weight, age, and the like, and cannot be generalized, the dosage is generally about 0.001 mg to about 2.0 g, based on the active ingredient, per day for an adult.

A therapeutic agent for wounds of the present invention is generally safely administered to a mammal (e.g., rat, mouse, guinea pig, rabbit, sheep, horse, swine, bovine, monkey, human) in a way such that a substance that suppresses the expression or function of PDLIM2 will be delivered to the wounded site.

Using a therapeutic agent for wounds of the present invention, wound healing reactions can be promoted. In particular, as shown in Examples below, inhibiting the expression or function of PDLIM2 promotes differentiation into myofibroblasts, which are important to wound contraction. For this and other reasons, a therapeutic agent for wounds of the present invention has an excellent effect in promoting wound contraction (an effect in reducing the wound area). Therefore, a therapeutic agent for wounds of the present invention is useful as a pharmaceutical for the treatment of various wounds (e.g., pressure ulcers, postoperative infections, diabetic ulcers, burns, corneal ulcers that accompany dry eyes, and the like).

(2. Screening Method)

The present invention provides a screening method for a substance capable of treating wounds, comprising determining whether or not a test substance is capable of suppressing the expression or function of PDLIM2, a substance obtained by the screening method, and an agent containing the substance.

In the screening method of the present invention, a substance that suppresses the expression or function of PDLIM2 can be obtained as a substance capable of treating wounds or a candidate substance for a therapeutic drug for wounds.

The test material subjected to the screening method may be any compound or composition; examples include nucleic acids (e.g., nucleosides, oligonucleotides, polynucleotides), saccharides (e.g., monosaccharides, disaccharides, oligosaccharides, polysaccharides), lipids (e.g., saturated or unsaturated linear, branched and/or cyclic fatty acids), amino acids, proteins (e.g., oligopeptides, polypeptides), organic low molecular compounds, compound libraries prepared using combinatorial chemistry technology, random peptide libraries prepared by solid phase synthesis or the phage display method, naturally occurring ingredients (e.g., ingredients derived from microorganisms, animals, plants, marine organisms and the like), foods, drinking water, and the like.

The screening method of the present invention can be performed in any way, as far as it enables a determination of whether or not the test substance is capable of suppressing the expression or function of PDLIM2. For example, the screening method of the present invention can be performed on the basis of:

1) a measurement of the expression of PDLIM2 using cells permitting a measurement of the expression of PDLIM2,
2) a measurement of a function of PDLIM2 using a reconstructed system permitting a measurement of function of PDLIM2,
3) a measurement of a function of PDLIM2 using a cell system enabling a measurement of a function of PDLIM2,
4) a measurement of the expression or function of PDLIM2 using an animal, and the like.

In 1) above, the screening method using cells permitting a measurement of the expression of PDLIM2 can comprise, for example, the following steps (a) to (c):

(a) the step of bringing into contact with each other a test substance and cells permitting a measurement of the expression of PDLIM2;
(b) the step of measuring the amount of PDLIM2 expressed in cells contacted with the test substance, and comparing this amount expressed with the amount of PDLIM2 expressed in control cells not contacted with the test substance;
(c) the step of selecting a test substance that suppresses the amount of PDLIM2 expressed on the basis of the results of the comparison in (b) above.

In the step (a) in the above-described method, the test substance is brought into contact with cells permitting a measurement of the expression of PDLIM2. The contact of the test substance with the cells permitting a measurement of the expression of PDLIM2 can be performed in a medium.

Cells permitting a measurement of the expression of PDLIM2 are cells that permit a direct or indirect evaluation of the expression level of a PDLIM2 product (e.g., transcription product, translation product). The cells permitting a direct measurement of the expression level of a PDLIM2 product can be PDLIM2 expressing cells, whereas the cells permitting an indirect evaluation of the expression level of the PDLIM2 product can be cells permitting a reporter assay for the transcriptional regulatory region of the PDLIM2 gene. The cells permitting a measurement of the expression of PDLIM2 can be mammalian cells.

The PDLIM2 expressing cells may be any cells that potentially express PDLIM2. Such cells can be easily identified by those skilled in the art; useful cells include primary culture cells, cell lines induced from the primary culture cells, commercially available cell lines, cell lines that can be obtained from cell banks, and the like. It is also preferable to use fibroblasts or immune cells such as macrophages as PDLIM2 expressing cells.

The cells permitting a reporter assay for the transcriptional regulatory region of the PDLIM2 gene are cells comprising the transcriptional regulatory region of the PDLIM2 gene and a reporter gene operably linked to the region. The transcriptional regulatory region of the PDLIM2 gene and the reporter gene can be inserted into an expression vector. The transcriptional regulatory region of the PDLIM2 gene is not particularly limited, as far as the region is capable of regulating the expression of PDLIM2; examples include a region between the transcription initiation point of each PDLIM2 gene and about 2 kbp upstream thereof, a region consisting of a base sequence resulting from deletion, substitution or addition of 1 or more bases in the base sequence of the region, and having the capability of regulating the transcription of these PDLIM2, and the like. The reporter gene may be any gene that encodes a detectable protein or an enzyme that catalyzes the production of a detectable substance; examples include the GFP (green fluorescence protein) gene, GUS (β-glucuronidase) gene, LUC (luciferase) gene, CAT (chloramphenicol acetyltransferase) gene and the like.

The cells to which the transcriptional regulatory region of the PDLIM2 gene and a reporter gene operably linked to the region are not particularly limited, as far as the regulatory function for the transcription of the PDLIM2 gene can be evaluated, i.e., the amount of the reporter gene expressed can be quantitatively analyzed. However, PDLIM2 expressing cells are preferred as the cells for transfer of the reporter gene because the cells express a physiological transcriptional regulatory factor for PDLIM2 and is thought to be more appropriate for an evaluation of the regulation of the expression of PDLIM2.

A medium in which a test substance and cells permitting a measurement of the expression of PDLIM2 are brought into contact with each other is chosen as appropriate according to the choice of cells used and the like; examples include minimal essential medium (MEM), Dulbecco's modified essential medium (DMEM), RPMI1640 medium, 199 medium and the like containing about 5 to 20% fetal bovine serum. Cultivation conditions are also determined as appropriate according to the choice of cells used and the like; for example, the pH of the medium is about 6 to about 8, cultivation temperature is generally about 30 to about 40° C., and cultivation time is about 12 to about 72 hours.

In the step (b) in the above-described method, the amount of PDLIM2 expressed in the cells contacted with the test substance is first measured. This measurement can be performed by one of the above-described methods known per se, in view of the choice of cells used and the like. When the cells permitting a measurement of the expression of PDLIM2 are cells permitting a reporter assay for the PDLIM2 transcriptional regulatory region, the amount of PDLIM2 expressed can be measured on the basis of the signal intensity of the reporter.

Subsequently, the amount of PDLIM2 expressed in the cells contacted with the test substance is compared with the amount of PDLIM2 expressed in control cells not contacted with the test substance. This comparison of the amounts expressed is preferably performed on the basis of the presence or absence of a significant difference. Although the amount of PDLIM2 expressed in the control cells not contacted with the test substance may be measured before or simultaneously with the measurement of the amount of PDLIM2 expressed in the cells contacted with the test substance, it is preferable, from the viewpoint of experimental accuracy and reproducibility, that the former amount expressed be a simultaneously measured amount expressed.

In the step (c) in the above-described method, a test substance that decreases the amount of PDLIM2 expressed is selected. A test substance that decreases the amount of PDLIM2 expressed (suppresses the expression of PDLIM2) can be selected as a substance capable of treating wounds, and is useful as a candidate substance for a therapeutic drug for wounds. In particular, a test substance that decreases the amount of PDLIM2 expressed is expected to have an excellent effect in promoting wound contraction (an effect in reducing the wound area).

As mentioned in 2) above, a reconstructed system enabling a measurement of a function of PDLIM2 refers to a non-cultured cell system enabling an evaluation of the suppression of a function of PDLIM2 by the test substance, and comprising PDLIM2 (protein) and other factors (e.g., proteins).

In an embodiment, the screening method of the present invention using a reconstructed system enabling a measurement of a function of PDLIM2 can be performed by determining whether or not the test substance suppresses the capability of forming a complex containing PDLIM2 and a binding partner thereof (e.g., Smad2, Smad3). As such, the screening method can comprise, for example, the following steps (a1) to (c1):

(a1) the step of bringing into contact with each other a test substance, PDLIM2, and a binding partner thereof;
(b1) the step of measuring the amount of the complex containing PDLIM2 and a binding partner thereof when contacted with the test substance, and comparing this amount of the complex with the amount of the complex when not contacted with the test substance;
(c1) the step of selecting a test substance that suppresses the amount of the complex containing PDLIM2 and a binding partner thereof on the basis of the results of the comparison in (A) above.

In the step (a1) in the above-described method, a test substance, PDLIM2, and a binding partner thereof are brought into contact with each other in an assay system enabling the formation of a complex containing PDLIM2 and a binding partner thereof. The binding partner is exemplified by Smad2 and Smad3. One or both of PDLIM2 and a binding partner thereof may have been labeled in order to facilitate the detection of a complex thereof. Examples of labeling methods include labeling with labeling substances (e.g., fluorescent substances such as FITC and FAM, luminescent substances such as luminol, luciferin, and lucigenin, radioisotopes such as $^{3}H$, $^{14}C$, $^{32}P$ $^{35}S$, and $^{123}I$, affinity substances such as biotin and streptavidin), and fusion with a protein that can be encoded by a reporter gene. In this assay system, cell homogenates comprising PDLIM2 and/or a binding partner thereof and the like (e.g., homogenates of cells transfected with a PDLIM2 expression vector and/or a PDLIM2 binding partner expression vector) can also be used.

In the step (b1) in the above-described method, the amount of the complex when contacted with the test substance is first measured. The complex containing PDLIM2 and a binding partner thereof is exemplified by a complex containing PDLIM2 and Smad2, a complex containing PDLIM2 and Smad3, a complex containing PDLIM2, Smad2 and Smad3, and the like. This measurement can be performed by a method known per se; examples include immunological techniques (e.g., immunoprecipitation, ELISA), interaction analyses based on surface plasmon resonance (e.g., use of Biacore™).

Subsequently, the amount of the complex when contacted with the test substance is compared with the amount of the complex when not contacted with the test substance. This comparison of the amounts of the complex is preferably performed on the basis of the presence or absence of a significant difference. Although the amount of the complex not contacted with the test substance may be measured before or simultaneously with the measurement of the amount of the complex when contacted with the test substance, it is preferable, from the viewpoint of experimental accuracy and reproducibility, that the former amount of the complex be a simultaneously measured amount of the complex.

In the step (c1) in the above-described method, a test substance that decreases the amount of the complex is selected. A test substance that decreases the amount of the complex containing PDLIM2 and a binding partner thereof (e.g., Smad2, Smad3) can be selected as a substance capable of treating wounds, and is useful as a candidate substance for a therapeutic drug for wounds. In particular, a test substance that decreases the amount of the complex containing PDLIM2 and Smad2 or Smad3 is expected to have an excellent effect in promoting wound contraction (an effect in reducing the wound area).

In another embodiment, the screening method of the present invention using a reconstructed system enabling a measurement of a function of PDLIM2 can be performed by, for example, determining whether or not the test substance is capable of suppressing the ubiquitination of Smad2 or Smad3 by PDLIM2. As such, the screening method can comprise, for example, the following steps (a2) to (c2):

(a2) the step of bringing into contact with each other a test substance, PDLIM2, Smad2 or Smad3, and factors required for the ubiquitination reaction;
(b2) the step of measuring the amount of ubiquitinated Smad2 or Smad3 when contacted with the test substance, and comparing the amount of ubiquitinated Smad2 or Smad3 with the amount of ubiquitinated Smad2 or Smad3 when not contacted with the test substance;
(c2) the step of selecting a test substance that suppresses the amount of ubiquitinated Smad2 or Smad3 on the basis of the results of the comparison in (b2) above.

In the step (a2) in the above-described method, a test substance, PDLIM2, Smad2 or Smad3, and factors required for the ubiquitination reaction are brought into contact with each other in an assay system enabling the ubiquitination of Smad2 or Smad3. Examples of factors required for the ubiquitination reaction include ubiquitin, E1, and E2.

In the step (b2) in the above-described method, the amount of ubiquitinated Smad2 or Smad3 when contacted with the test substance is first measured. This measurement of the amount of ubiquitinated Smad2 or Smad3 can be performed by a method known per se; examples include immunological techniques such as Western blotting.

Subsequently, the amount of ubiquitinated Smad2 or Smad3 when contacted with the test substance is compared with the amount of ubiquitinated Smad2 or Smad3 when not contacted with the test substance. This comparison of the amounts of ubiquitinated Smad2 or Smad3 is preferably performed on the basis of the presence or absence of a significant difference. Although the amount of ubiquitinated Smad2 or Smad3 when not contacted with the test substance may be measured before or simultaneously with the measurement of the amount of ubiquitinated Smad2 or Smad3 when contacted with the test substance, it is preferable, from the viewpoint of experimental accuracy and reproducibility, that the former amount of ubiquitinated Smad2 or Smad3 be a simultaneously measured amount of ubiquitinated Smad2 or Smad3.

In the step (c2) in the above-described method, a test substance that decreases amount of ubiquitinated Smad2 or Smad3 (i.e., suppresses the ubiquitination of Smad2 or Smad3) is selected. A test substance that decreases the amount of ubiquitinated Smad2 or Smad3 can be selected as a substance capable of treating wounds, and is useful as a candidate substance for a therapeutic drug for wounds. In particular, a test substance that decreases amount of ubiquitinated Smad2 or Smad3 (i.e., suppresses the ubiquitination of Smad2 or Smad3) is expected to have an excellent effect in promoting wound contraction (an effect in reducing the wound area). For details of the ubiquitination assay, see, for example, Tanaka T. et al, Immunity 22: 729-736 (2005).

In 3) above, the screening method wherein a function of PDLIM2 is measured using a cell system enabling a measurement of a function of PDLIM2 can be performed by, for example, determining i) whether or not the test substance suppresses the ubiquitination of Smad2 or Smad3 by PDLIM2, or ii) whether or not the test substance decreases the amount of the complex containing PDLIM2 and a binding partner thereof (e.g., Smad2, Smad3). As such, the screening method can comprise, for example, the following steps (a) to (c):

(a) the step of bringing into contact with each other a test substance and PDLIM2 expressing cells;
(b) the step of measuring the functional level of PDLIM2 in the cells contacted with the test substance, and comparing this functional level with the functional level in control cells not contacted with the test substance;
(c) the step of selecting a test substance that suppresses the functional level of PDLIM2 on the basis of the results of the comparison in (b) above.

In the step (a) in the above-described method, a test substance is brought into contact with PDLIM2 expressing cells. This contact of the test substance with the PDLIM2 expressing cells can be performed in a medium. The PDLIM2 expressing cells used here can be cells capable of expressing PDLIM2 to the extent that enables an assay of PDLIM2 at the protein level. Examples of preferred PDLIM2 expressing cells include cells (e.g., mast cells, T cells, fibroblasts) transfected with a PDLIM2 expression vector and/or an Smad2 expression vector and/or an Smad3 expression vector and cells that naturally express PDLIM2 and Smad2 and/or Smad3 (e.g., fibroblasts, immune cells such as macrophages). The contact of the test substance with the PDLIM2 expressing cells can be performed in a medium.

In the step (b) in the above-described method, the functional level of PDLIM2 in the cells contacted with the test substance is first measured. For example, the determination i) can be made by measuring the amount of ubiquitinated Smad2 or Smad3 (see Examples and Tanaka T. et al, Immunity 22: 729-736 (2005)). The determination ii) can be made using a two-hybrid system, as well as by the method (b1) in 2) above. The comparison of the functional levels in this step (b) can be performed in the same manner as the above-described method 2).

In the step (c) in the above-described method, a test substance that decreases the functional level of PDLIM2 (suppresses a function of PDLIM2) is selected. A test substance that decreases the functional level of PDLIM2 can be selected as a substance capable of treating wounds, and is useful as a candidate substance for a therapeutic drug for wounds. In particular, a test substance that decreases the functional level of PDLIM2 is expected to have an excellent effect in promoting wound contraction (an effect in reducing the wound area).

In 4) above, the screening method of the present invention using an animal can comprise, for example, the following steps (a) to (c):

(a) the step of administering a test substance to an animal;
(b) the step of measuring the amount or functional level of PDLIM2 expressed in the animal receiving the administration of the test substance, and comparing this amount expressed or functional level with the amount or functional level of PDLIM2 expressed in a control animal not receiving the administration of the test substance;
(c) the step of selecting a test substance that suppresses the amount or functional level of PDLIM2 expressed on the basis of the results of the comparison in (b) above.

This methodology may have only the steps (b) and (c) as being essential thereto.

In the step (a) in the above-described method, optionally chosen warm-blooded animals, for example, the aforementioned mammals, can be used. Administration of a test substance to an animal can be performed by a method known per se.

In the step (b) in the above-described method, the measurement of the amount or functional level of PDLIM2 expressed can be achieved by a method known per se. For example, the amount or functional level of PDLIM2 expressed in immune cells isolated or collected from an animal can be measured by the same methodology as the step (b) in the above-described methods 1) to 3). The comparison of the amounts expressed in this step (b) and the selection in the step (c) can also be performed in the same manner as the methodologies 1) to 3) above.

(3. Others)

The present invention provides a complex containing PDLIM2 and Smad2 or Smad3, a method of preparing the same, and a method of detecting the same. The complex containing PDLIM2 and Smad2 or Smad3 is exemplified by a complex containing PDLIM2 and Smad2, a complex containing PDLIM2 and Smad3, a complex containing PDLIM2, Smad2, and Smad3, and the like. Complexes of the present invention are useful in the screening method of the present invention.

Smad2 and Smad3 are publicly known transcription factors that mediate TGFβ signaling.

As mentioned herein, Smad2 and Smad3 are generally those derived from a warm-blooded animal (mammal or bird). Examples of the mammal include, but are not limited to, laboratory animals such as mice, rats, hamsters, guinea pigs, and other rodents, and rabbits; domestic animals such as swines, bovines, goat, horses, sheep, and minks; companion animals such as dogs and cats; and primates such as humans, monkeys, cynomolgus monkeys, rhesus monkeys, marmosets, orangutans, and chimpanzees. Examples of the bird include chicken, quails, domestic ducks, geese, turkeys, emus, ostriches, guinea fowls, pigeons and the like. Smad2 and Smad3 are preferably derived from a mammal, more preferably from a primate (human etc.) or a rodent (mouse etc.).

In a complex of the present invention, the strength of the binding between PDLIM2 and Smad2 or Smad3 is such that PDLIM2 and Smad2 or Smad3 can be co-precipitated in an immunoprecipitation test.

PDLIM2, Smad2, and Smad3 can be proteins that can be collected from cells that naturally express the desired protein, or recombinant proteins. PDLIM2 can be prepared by a method known per se; for example, a) PDLIM2 may be collected from naturally occurring PDLIM2 expressing cells (e.g., macrophages, dendritic cells, fibroblasts, T cells, B cells), b) PDLIM2 produced by a transformant prepared by transferring a PDLIM2 expression vector into host cells (e.g., bacteria belonging to the genus Escherichia, bacteria belonging to the genus Bacillus, yeast, insect cells, insects, animal cells) may be collected from the transformant, and c) PDLIM2 may be synthesized using a cell-free system using a rabbit reticulocyte lysate, wheat germ lysate, Escherichia coli lysate or the like. Smad2 and Smad3 can be prepared in the same manner. PDLIM2, Smad2, and Smad3 are isolated or purified as appropriate by methods based on differences in solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography and use of antibodies; methods based on differences in hydrophobicity, such as reverse phase high performance liquid chromatography; methods based on differences in isoelectric point, such as isoelectric focusing; combinations thereof, and the like.

A complex of the present invention can be produced by mixing the PDLIM2 and Smad2 or Smad3 thus obtained in an appropriate buffer solution to bind them together. The complex obtained is preferably further isolated or purified by removing proteins other than the desired complex by gel filtration and the like.

The detection of a complex can be performed by an immunological technique using an anti-PDLIM2 antibody and/or anti-Smad2 antibody or anti-Smad3 antibody.

The present invention also provides cells that naturally express Smad2 or Smad3 and have a PDLIM2 expression vector incorporated, cells that naturally express PDLIM2 and have an Smad2 or Smad3 expression vector incorporated, and cells having one or two incorporated vectors for expression of PDLIM2 and Smad2 or Smad3 (e.g., a combination of expression vectors, a co-expression vector). These cells of the present invention are useful in the screening of the present invention.

The contents disclosed in any publication cited herein, including patents and patent applications, are hereby incorporated in their entireties by reference, to the extent that they have been disclosed herein.

The present invention is explained in more detail in the following by referring to Examples, which are not to be construed as limitative.

EXAMPLES

Example 1

Method (Plasmids)

For preparing the Smad expression constructs, the coding sequence of murine smad2, 3 or 4 was inserted into pCMV-Myc (Clontech). The expression plasmid for c-Myc-tagged PDLIM2 was generated by subcloning the coding region of murine Pdlim2 into pCMV-Myc (Clontech). For HA-tagged PDLIM2 construct, PCR-amplified HA-tag plus the coding region of murine pdlim2 replaced c-Myc-tagged pdlim2 of PDLIM2-pCMV-Myc construct. The pTARE luciferase reporter construct was purchased from STRATAGENE.

(Reagents and Antibodies)

Human recombinant TGFβ was purchased from WAKO chemicals. Anti-Smad2 and Smad4 antibodies were purchased from Cell Signaling Technology. Anti-Smad3 antibody was purchased from abcam. Anti-HSP90, Sp1 and DNA polymerase δ catalytic subunit antibodies were purchased from Santa Cruz Biotechnology. Anti-actin antibody was purchased from Sigma. Anti-Myc antibody was purchased from MBL.

(Wound Healing Experiments)

The generation of Pdlim2$^{-/-}$ mice has been described previously (Tanaka et al, Nat. Immunol. 8, 584-591, 2007). Mice were maintained under SPF (specific pathogen-free) conditions and used after backcrossing with Balb/c at least seven times. All experiments were in accordance with guidelines approved by RIKEN Yokohama Institute Animal Use Committee. Full-thickness cutaneous excisional wounds were made on the center of the dorsal skin (6 mm diameter). The wound areas were measured at day 0, 3, 5 and 7 post wounding. The wound tissue was collected at day 7, fixed in 10% formaldehyde, embedded in paraffin, sectioned and stained with hamatoxylin and eosin (H&E).

(Collagen Gel Contraction Assay)

Collagen gel culture kit (Nitta Gelatin Inc.) was used for this assay. Type I collagen solution was prepared as manufacture's protocol. Collagen solution was then mixed with wild-type and PDLIM2-deficient embryonic fibroblasts, pored into 12-well cell culture plate (1 ml in each well) and gelled at 37° C. for 30 min. Serum free DMEM (1 ml) was further pored on the gel. After 12 hours of incubation, the gel was separated from each well, floated and incubated in the presence or absence of TGFβ. The surface area of the gel was measured at 0, 8 and 24 hours after gel release.

(Cells, Transfection, Reporter Assay)

Mouse embryonic fibroblasts (MEF) were prepared from 13.5 dpc embryos and cultured in DMEM supplemented with indicated percentage of FCS. Normal human fibroblasts were purchased from Lonza Walkersville Inc and cultured with Fibroblast culture media kit (Lonza) or DMEM supplemented with 10% FCS. 293T cells were maintained in DMEM supplemented with 10% FCS. Effectene transfection reagent (QIAGEN) was used for transient transfection. For the reporter assay, MEF were transfected with the pTARE luciferase construct and expression plasmids encoding wild-type or frame shift mutant PDLIM2 molecules. Total amounts of transfected DNA were kept constant by supplementing with control plasmids. Luciferase activity was measured according to the manufacturer's protocol (Promega).

(Subcellular Fractionation, Immunoprecipitation and Immunoblot)

All lysis buffers used for immunoblot analysis contained a proteinase inhibitor cocktail (Roche). Cytoplasmic and nuclear extracts were prepared as follows. Cells were lysed on ice for 10 min with hypotonic buffer (20 mM HEPES pH 8.0, 10 mM KCl, 1 mM MgCl$_2$, 0.1% Triton X-100, 20% glycerol). After centrifugation (5,000 rpm, 1 min), supernatants were collected and used as cytoplasmic fractions. The pellets were next lysed on ice for 20 min after brief vortexing with hypertonic buffer (20 mM HEPES pH 8.0, 1 mM EDTA, 20% glycerol, 0.1% Triton X-100, 400 mM NaCl). After centrifugation (15,000 rpm, 5 min), supernatants were collected and used as nuclear fractions. The purity of the obtained fractions was confirmed using anti-HSP90 (for cytoplasm) or anti-Sp1 (for nuclear fraction). For immunoprecipitation, whole cell extracts were prepared by lysing cells in buffer (250 mM NaCl, 50 mM Tris pH 8.0 and 0.5% NP-40). Extracts were incubated with anti-Myc antibody plus protein G-Sepharose (Amersham Bioscience), washed four times and subjected to immunoblot analysis with the indicated antibodies.

(Ubiquitination Assay)

293T cells were transfected with expression plasmids encoding c-Myc-tagged Smad2, 3 or 4, His-tagged ubiquitin and HA-tagged WT or frame-shift mutant PDLIM2 molecules. Transfected cells were extracted under denaturing conditions with buffer containing 6 M guanidium-HCl, Na$_2$HPO$_4$/NaH$_2$PO$_4$, pH8.0, 10 mM imidazole. Extracts were incubated with Ni-NTA agarose (Novagen) for 3 h and then washed with buffer containing 25 mM Tris pH 6.8, 20 mM imidazole. Purified proteins were subjected to immunoblot with anti-c-Myc antibody.

(Myofibroblasts Differentiation Experiments)

Wild-type and PDLIM2-deficient fibroblasts were plated in DMEM supplemented with 10% FCS. After 24 hours, media were changed to FCS free DMEM and further cultured for 24 hours. Cells were then stimulated with human TGFβ (10 ng/ml) for 3 days. Morphology of the cells was analyzed and the percentages of the spindle-shaped cells were calculated.

(RT-PCR Analysis)

Wild-type and PDLIM2-deficient fibroblasts were plated in FCS free DMEM and cultured for 24 hours. Cells were then stimulated with human TGFβ (10 ng/ml) for 3 and 6 hours. Total RNA was extracted using RNeasy micro RNA extraction kit (Qiagen). cDNA was synthesized using PrimeScript RT reagent kit (TAKARA) and subjected to quantitative real-time PCR analysis using a 7000 Sequence detector (Applied Biosystems). Reactions were performed using primers against 18S rRNA (internal control) and α-smooth muscle actin (TaqMan Gene Expression Assays, Applied Biosystems).
(siRNA)
The double strand siRNAs were synthesized and modified into Staelth siRNA (Invitrogen). The target sites for siRNA were selected using BLOCK-iT RNAi designer, on-line tool from Invitrogen. The sequences of siRNA oligonucleotides are as follows;

```
siRNA against mouse PDLIM2:
5'-CAGAGATTTCCACACACCCATCATT-3'    (SEQ ID NO: 5)

control siRNA(mouse):
5'-CAGTTTACACCCACATACCCGAATT-3'    (SEQ ID NO: 6)

siRNA against human PDLIM2:
5'-TGATGGCCACGATTATGTCTCCAGG-3'    (SEQ ID NO: 7)
```

Stealth RNAi negative control duplex (Invitrogen, Cat#12935-115) was used as a control in human fibroblasts. siRNA was transfected into murine embryonic fibroblasts or normal human dermal fibroblasts by Lipofectamine RNAiMAX (Invitrogen).
[Results]
(Promotion of Wound Healing Response in PDLIM2-Deficient Mouse)
The dorsal skin of the mouse was excised in a circle (diameter 6 mm) and repairing and healing process of this part was observed for 7 days. The wounds of wild-type and PDLIM2-deficient mice at day 7 are shown in FIG. 1a. The wound size of PDLIM2-deficient mouse at day 7 was clearly shrunk as compared to wild-type mouse, suggesting that wound healing was markedly promoted in PDLIM2-deficient mouse. In PDLIM2-deficient mouse, the hair growth around the wound was remarkably promoted. FIG. 1b shows the size of the wounds of wild-type mouse and PDLIM2-deficient mouse over time. In PDLIM2-deficient mouse, particularly remarkable contraction of the wound area was observed from 5 days after wounding. Then, the skin and subcutaneous tissue of the wound were histologically observed. As a result, PDLIM2-deficient mouse and wild-type mouse showed no difference in the formation of granulation tissue, angiogenesis, and reepithelialization, and only the promotion of macroscopic contraction of wound was clarified in PDLIM2-deficient mouse (FIG. 1c). Therefore, in vitro wound contraction model experiments were performed using primary embryonic fibroblasts derived from wild-type and PDLIM2-deficient mice. The previous studies have clarified that the wound contraction in this experiment system is promoted by TGFβ stimulation. Thus, fibroblasts were embedded in collagen gel solution, and cultured for 12 hr. Then the gel was detached from the culture plate and floated, and the surface area of the collagen gel was measured in the presence or absence of TGFβ over time, based on which the level of contraction of the gel containing respective fibroblasts was evaluated. In the gel in which fibroblasts derived from PDLIM2-deficient mouse were embedded, the contraction was significantly promoted by stimulation with TGFβ as compared to wild-type mouse (FIG. 1d). Therefrom, it was suggested that TGFβ dependent signal transduction was promoted in PDLIM2-deficient mouse. Therefore, how PDLIM2 regulates TGFβ dependent signal transduction was analyzed next.

Figure 2:
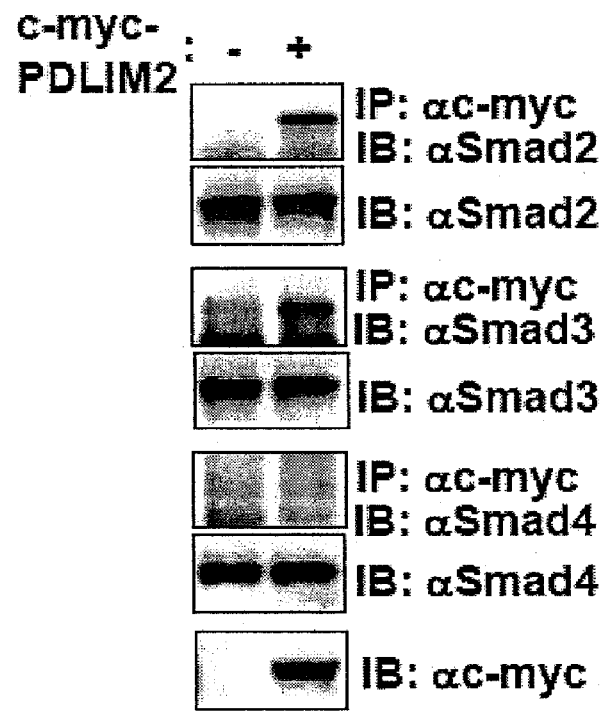
FIG. 2 shows that PDLIM2 binds to Smad2/3 and negatively regulates the TGFβ-Smad-mediated transcription. (a) An interaction between c-Myc-tagged PDLIM2 and an endogenous Smad transcription factors; 293T cells were transfected with or without a c-Myc-tagged PDLIM2 expression plasmid (c-Myc PDLIM2) and treated to obtain whole cell extracts, which were immunoprecipitated (IP) with anti-c-Myc antibody, and immunoblotted (IB) with anti-Smad2, 3 or 4 antibody. (b) Luciferase activity in mouse embryonic fibroblasts; with or without a plasmid that encodes PDLIM2, the cells were transfected with a plasmid that encodes a TARE luciferase reporter (pTARE-Luc), after which the cells were stimulated with human TGFβ (10 ng/ml) for 6 hours and assayed.
Figure 2:
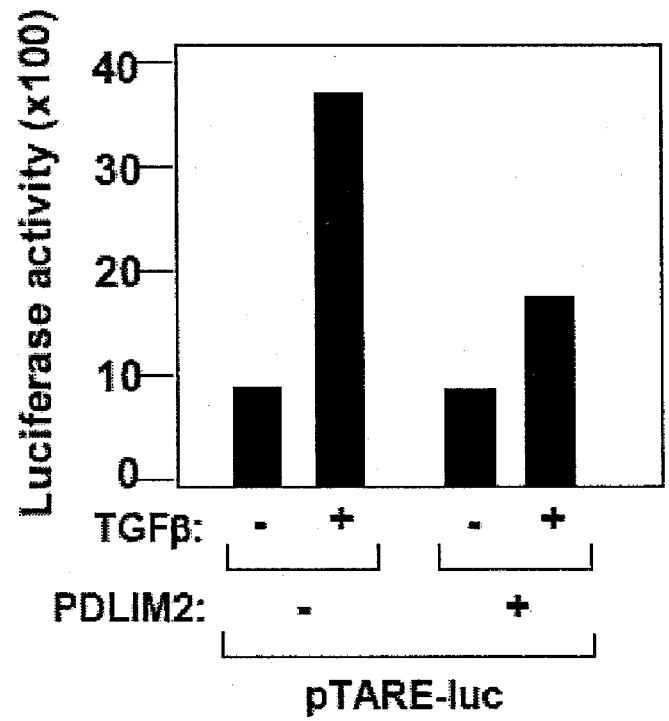
Figure 3:
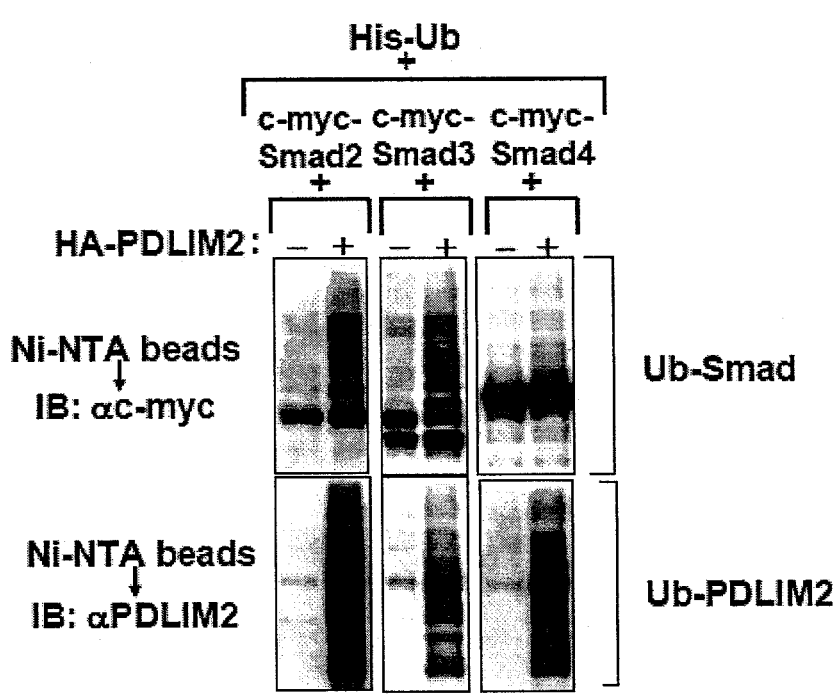
FIG. 3 shows that PDLIM2 promotes the polyubiquitination and degradation of Smad2 and Smad3 but does not promote the same of Smad4. (a) Smad ubiquitination assay in 293T cells; with or without an HA-tagged PDLIM2 expression plasmid (HA-PDLIM2), 293T cells were transfected with a plasmid that encodes His-ubiquitin (His-Ub), c-Myc-tagged Smad2, 3 or 4. The ubiquitinated protein was purified using Ni-NTA beads, and immunoblotted with anti-c-Myc antibody for the ubiquitination of Smad (Ub-Smad), or with anti-PDLIM2 antibody for the self-ubiquitination of PDLIM2 (Ub-PDLIM2). (b) Effects of PDLIM2 on nuclear Smad2 and Smad3 in 293T cells; with or without a c-Myc-tagged PDLIM2 expression plasmid, 293T cells were transfected with a plasmid that encodes c-Myc-tagged Smad2 or Smad3, and analyzed by immunoblot with anti-c-Myc antibody.
Figure 3:
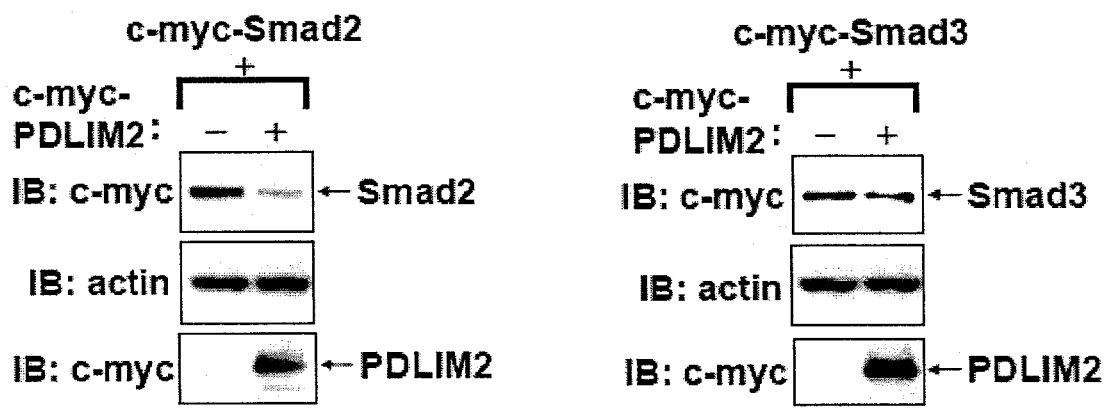
Figure 4:
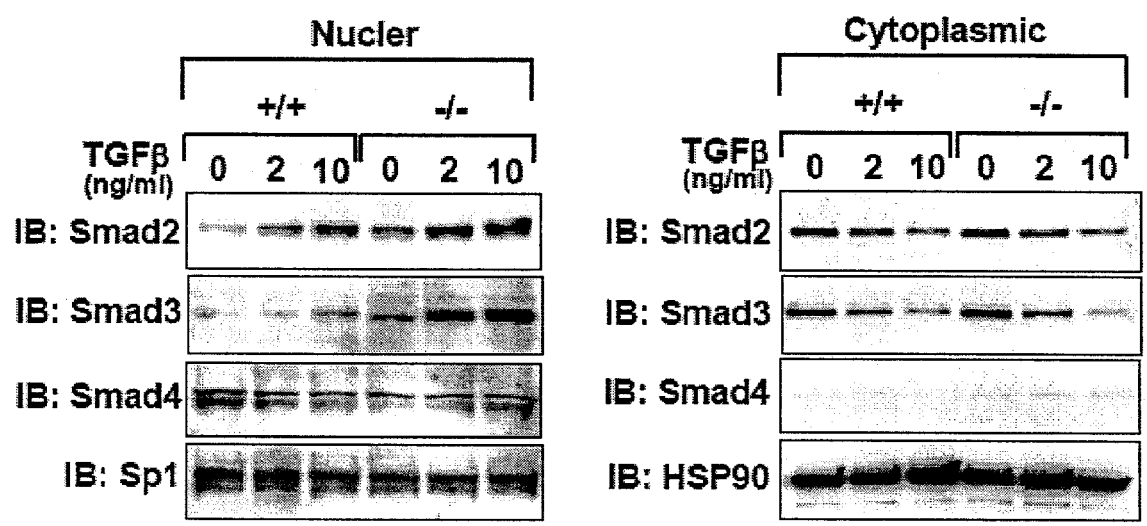
FIG. 4 shows Smad2/3 activation promoted in PDLIM2-deficient fibroblasts. Cytoplasmic (Cyt) or nuclear (Nuc) extracts from wild-type or PDLIM2-deficient fibroblasts, stimulated with human TGFβ (0, 2, 10 ng/ml) for 1 hour, were immunoblotted with anti-Smad2, 3 or 4 antibody. Anti-HSP90 antibody and anti-Sp1 antibody were served as controls.

(PDLIM2 Binds to Smad2/3 and Suppresses TGFβ Dependent Signal Transduction)
When TGFβ is bound to a receptor on the cellular surface, the receptor first phosphorylates directly the serine residues in transcription factors Smad2 and Smad3. The thus-activated Smad2/3 further forms a complex with Smad4, enters into the nucleus and induces expression of various target genes. It has been reported that these activated Smads are inactivated by ubiquitination and degradation, and several ubiquitin ligases in charge of the ubiquitination of Smad transcription factors have already been identified. Since PDLIM2 is a nuclear protein, and acts as an ubiquitin ligase for STAT4 and NF-κB, the possibility of its function as a nuclear ubiquitin ligase also for Smad was investigated.
Firstly, whether PDLIM2 is associated with these Smad transcription factors was studied using co-immunoprecipitation assay. c-Myc-tagged PDLIM2 was expressed in 293 cells, and a protein extract of the cells was immunoprecipitated with an antibody against c-Myc and blotted with antibodies against Smad2, 3 or 4, and binding of each Smad to PDLIM2 was examined. PDLIM2 was selectively associated with Smad2 and Smad3, and was not bound to Smad4 (FIG. 2a). Then, using a reporter assay, the effect of PDLIM2 on Smad dependent gene activation was examined. A luciferase reporter plasmid having three Smad binding sequences in the upstream was transfected into a fibroblast cell line. When the cells were stimulated with TGFβ, the reporter was activated. However, when PDLIM2 was co-expressed, activation of the reporter was significantly inhibited (FIG. 2b). Therefrom it was clarified that PDLIM2 acts suppressively to the activation of TGFβ dependent Smad activation.
(PDLIM2 Ubiquitinates and Degrades Smad2 and 3)
Next, whether PDLIM2 ubiquitinates these Smads was investigated. 293 cells were transfected with an expression vector for c-Myc tagged Smad2, 3 or 4 together with histidine-tagged ubiquitin expression vector and PDLIM2 expression vector or control vector. Histidine-labeled protein was purified from a protein extract of these cells using nickel NTA beads and ubiquitination of each Smad was detected using an anti-c-Myc antibody (FIG. 3a). While Smad2 and Smad3 were strongly ubiquitinated by co-expression of PDLIM2, Smad4 was hardly ubiquitinated. It is known that ubiquitinated protein is generally degraded by proteasome. Thus, whether PDLIM2 can induce degradation of Smad2 and 3 was examined. c-Myc tagged Smad2 and 3 were expressed in 293 cells together with PDLIM2 expression vector or control vector. Nuclear fraction was extracted from these cells, and the protein level of nuclear Smad2/3 was examined using an anti-c-Myc antibody (FIG. 3b). The protein levels of nuclear Smad2 and 3 were decreased due to the co-expression of PDLIM2. From the above results, it was clarified that PDLIM2 selectively binds to Smad2 and 3 and inactivates these transcription factors by ubiquitinating and degrading them; namely, PDLIM2 is an ubiquitin ligase for Smad2 and Smad3.
(Promotion of Activity of Smad2/3 in PDLIM2-Deficient Cells)
Furthermore, the effect of PDLIM2 on TGFβ-mediated Smad activation was investigated using PDLIM2-deficient mouse embryonic fibroblast. Wild-type fibroblasts and fibroblasts derived from PDLIM2-deficient mouse were stimulated with TGFβ (0, 2, 10 ng/ml) for 1 hr, and the cytoplasmic fraction and nuclear fraction were extracted. Using anti-Smad2, 3 and 4 antibodies, and the cytoplasmic and nuclear protein levels of each Smad were examined (FIG. 4). In PDLIM2-deficient fibroblasts, the protein levels of nuclear Smad2 and 3 significantly increased as compared to the cells derived from wild-type mouse. In contrast, the protein level of nuclear Smad4 did not show difference between these cells. Moreover, the protein levels of cytoplasmic Smad2 and 3 did not show difference between both cells (FIG. 4). These results suggest activation of Smad2/3 by TGFβ is promoted in PDLIM2-deficient cells. This is consistent with the above-mentioned finding that PDLIM2 is a nuclear ubiquitin ligase for Smad2/3.

(Promotion of Differentiation into Myofibroblast in PDLIM2-Deficient Cell)

Figure 5:
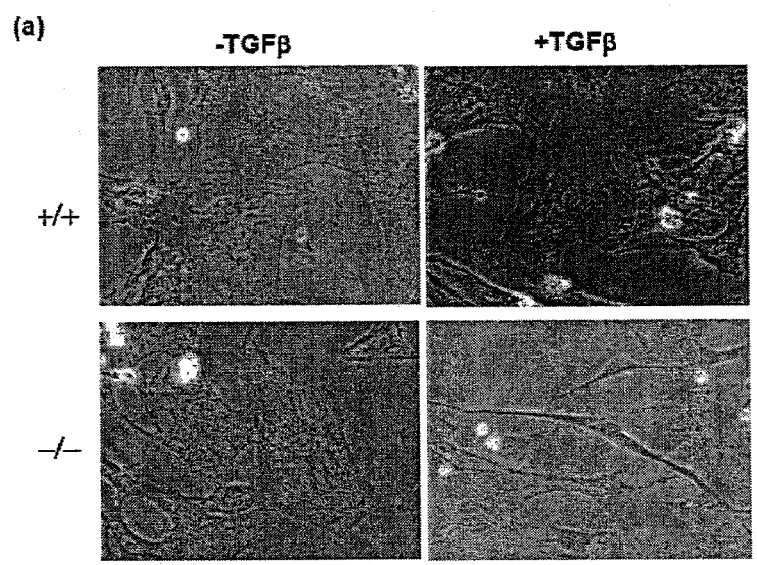
FIG. 5 shows differentiation into myofibroblasts promoted in PDLIM2-deficient fibroblasts. (a) Morphology of wild-type (+/+) fibroblasts and PDLIM2-deficient (−/−) fibroblasts, which were stimulated without or with human TGFβ (10 ng/ml) for 3 days. (b) Percentage of the spindle cells mentioned in (a). (c) Expression of α-smooth muscle actin (SMA) in wild-type and PDLIM2-deficient fibroblasts, which were stimulated with human TGFβ (10 ng/ml) for 0, 3 and 6 hours.
Figure 5:
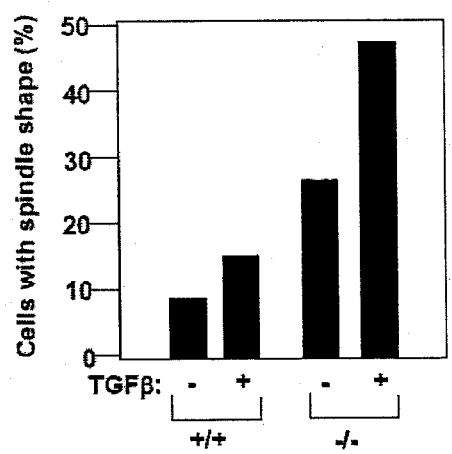
Figure 5:
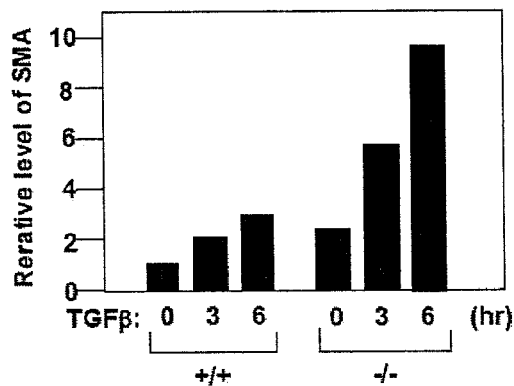

As mentioned above, differentiation of fibroblast in the granulation tissues into myofibroblast is important for wound contraction observed in the wound healing process. It has been clarified that TGFβ promotes such differentiation. Thus, wild-type fibroblasts and fibroblasts derived from PDLIM2-deficient mouse were cultured in the presence or absence of TGFβ, and differentiation of these cells into myofibroblasts was examined. Typical fibroblast takes a stellate appearance. When it is differentiated into myofibroblast, it takes a spindle form, with prominent projections from the cytoplasm. In the fibroblast derived from PDLIM2-deficient mouse, the ratio of cells with a spindle form significantly increased in the presence of TGFβ, as compared to wild-type cells (FIG. 5a, FIG. 5b). In addition, expression of α-smooth muscle actin, which is a differentiation marker of myofibroblast, was also promoted in the fibroblast derived from PDLIM2-deficient mouse (FIG. 5c). Therefrom it was clarified that TGFβ-dependent differentiation into myofibroblasts is promoted in PDLIM2-deficient cells.

(Promotion of Differentiation into Myofibroblast by siRNA Against PDLIM2)

Figure 6:
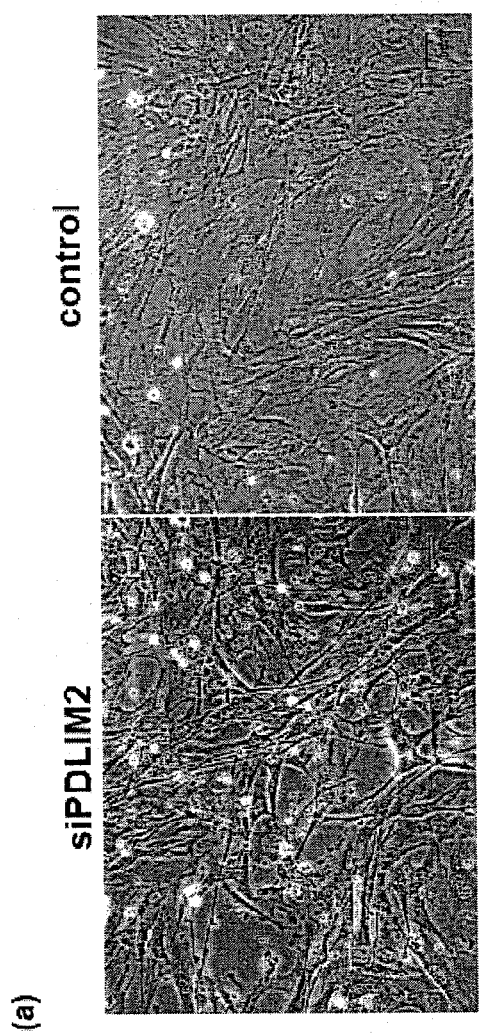
FIG. 6 shows myofibroblast differentiation promoted by PDLIM2 knockdown using an siRNA against mouse PDLIM2. (a) Morphology of fibroblasts transfected with the siRNA against PDLIM2 or control oligonucleotides. (b) Percentage of the spindle-shaped cells mentioned in (a). (c) Nuclear extracts from fibroblasts transfected with the siRNA against mouse PDLIM2 or control oligonucleotides, and stimulated with human TGFβ (10 ng/ml) for 1 hour, were immunoblotted with anti-Smad2 or Smad3 antibody; the anti-DNA polymerase δ (DNApol) were served as a control. (d) Percentage of spindle-shaped cells in normal human skin fibroblasts transfected with the siRNA against human PDLIM2 or a control oligonucleotides.
Figure 6:
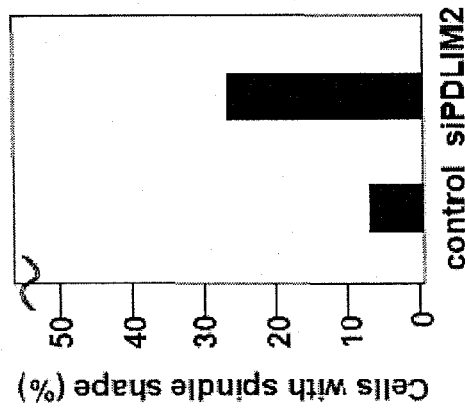
Figure 6:
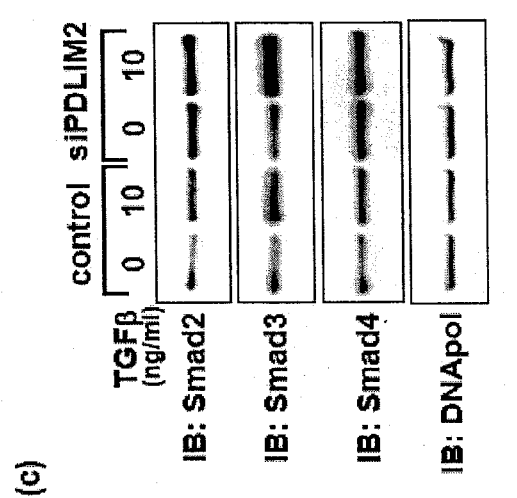
Figure 6:
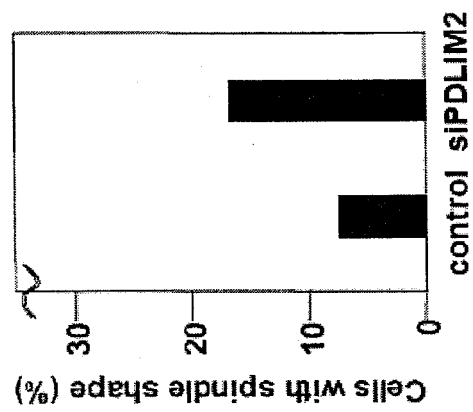

Next, PDLIM2 was knocked down in fibroblast using siRNA (RNA interference method), and the effect on the differentiation into myofibroblast was examined. First, siRNA against mouse PDLIM2 gene or control siRNA were transferred into fibroblasts derived from wild-type mouse. In the cells transferred with siRNA against PDLIM2, the ratio of cells with a spindle form significantly increased as compared to the cells transferred with control siRNA (FIG. 6a, FIG. 6b). In the cells transferred with siRNA against PDLIM2, moreover, the nuclear protein levels of Smad2 and Smad3 when stimulated with TGFβ were promoted as compared to the control cells (FIG. 6c). Therefrom it was suggested that siRNA against PDLIM2 suppresses degradation of Smad2 and Smad3 and promotes TGFβ dependent signal transduction, thereby promoting differentiation into myofibroblast. Moreover, siRNA against human PDLIM2 was prepared and transfected into normal diploid fibroblast derived from human skin. As a result, the ratio of cells with a spindle form significantly increased as compared to the cells transferred with control siRNA (FIG. 6d). Therefrom it was suggested that suppression of the expression or function of PDLIM2 promotes differentiation into myofibroblast even in human.

From the foregoing, it was clarified that PDLIM2 negatively regulates TGFβ-induced activation of Smad by ubiquitinating and degrading Smad2 and 3 as a nuclear ubiquitin ligase for these transcription factors. In wound healing response, it was suggested that PDLIM2 functions to terminate the wound healing response at an appropriate time point by negatively regulating TGFβ dependent signal transduction pathway so that the reaction will not proceed excessively. Accordingly, it was suggested that suppression of expression or function of PDLIM2 promotes the wound healing response (particularly, wound contraction).

Example 2

Double stranded siRNA was synthesized, and altered to stealth siRNA (Invitrogen). The siRNA target site was selected using BLOCK-iT RNAi designer, which is an online tool from Invitrogen. The siRNA oligonucleotide sequences used were as follows:

```
siRNA against mouse PDLIM2:
5'-CACACCTGTGAGAAATGCAGCGTCA-3'    (SEQ ID NO: 8)

control siRNA (mouse):
5'-CAGTTTACACCCACATACCCGAATT-3'    (SEQ ID NO: 6)
```

For the experiment including administration of siRNA to an individual mouse, Invivofectamine (Invitrogen) was used. Invivofectamine and siRNA (siRNA that specifically inhibits expression of PDLIM2 or control RNA) were mixed according to the manufacturer's protocol. After completion of the reaction, the solvent of the reaction product was substituted for 5% glucose using Amicon Ultra-15 Centrifugal Device with Ultracel-50 membrane (Amicon) to give an siRNA solution for administration.

Balb/c mouse was anesthetized, the back was shaved, and the skin of the back was excised in a circle (diameter about 7 mm) to produce a wound. The obtained siRNA solution (siRNA that specifically inhibits expression of PDLIM2 or control RNA) was dropped on the mucous membrane of the wound by 30 microliter (20 microgram as RNA) per mouse. The siRNA solution was absorbed by the mucous membrane of the wound in about 5-10 min. During the operation, the mouse did not move due to anesthesia. The long diameter and short diameter of the wound were measured over time, and the percentage relative to the wound area before the treatment was calculated.

Figure 7:
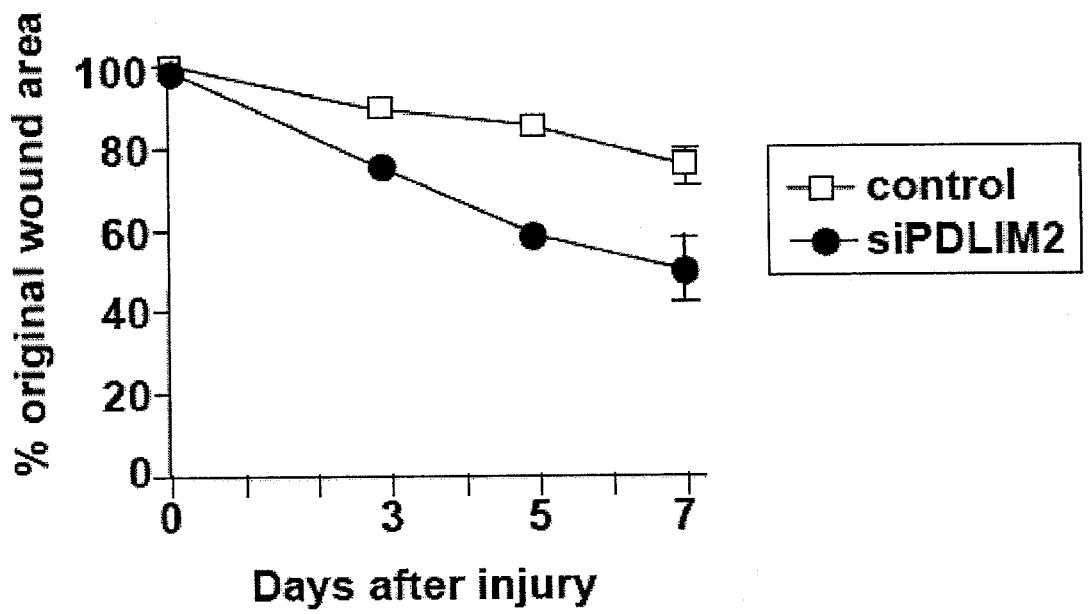
FIG. 7 shows wound healing reactions promoted by the siRNA that specifically suppresses the expression of PDLIM2. The axis of ordinates indicates relative values of wound area (percent values relative to pre-treatment wound area); the axis of abscissas indicates the number of days after wounding. Squares indicate a control group; solid circles indicate a group administered with the siRNA that specifically suppresses the expression of PDLIM2.
Figure 8:
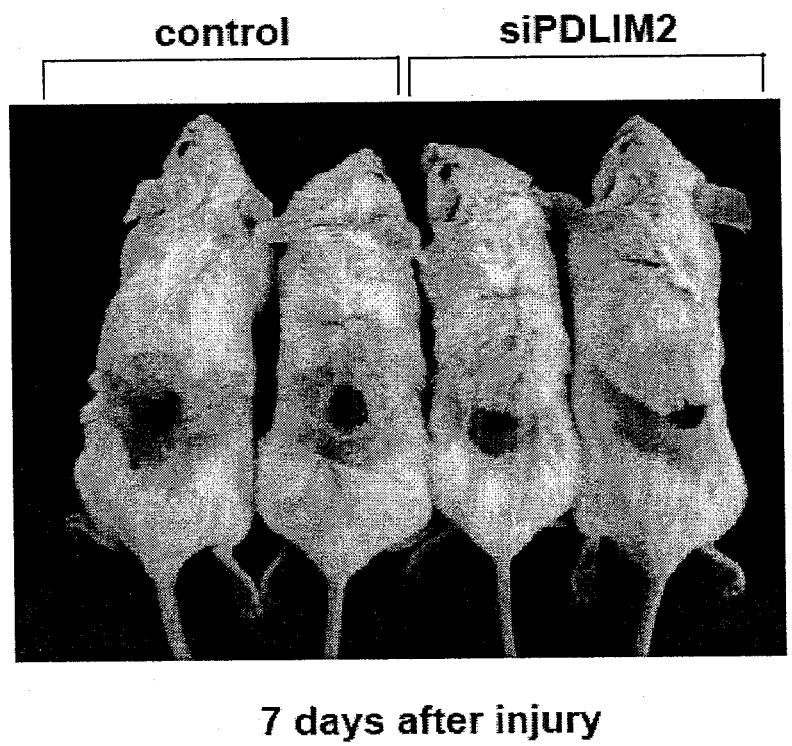
FIG. 8 shows a photograph of enhanced wounds contraction in mice treated with the siRNA that specifically suppresses the expression of PDLIM2 (7 days after wounding). siPDLIM2 indicates a group of mice administered with the siRNA that specifically suppresses the expression of PDLIM2.

FIG. 7 shows time-course changes of the wound area, and FIG. 8 shows the wound of the siRNA administration group or control group at day 7. The administration of siRNA against PDLIM2 promoted wound healing as compared to that of the control. In the group administered with siRNA against PDLIM2, the hair growth around the wound was remarkably promoted, and these effects were consistent with that of the phenotype of PDLIM2 knockout mouse (see Example 1).

From the foregoing results, it was shown that a wound healing response is promoted by suppressing the expression or function of PDLIM2.

Reference Example 1

Mouse embryonic fibroblasts were transfected with siRNA against mouse PDLIM2 (SEQ ID NO:5 (siPDLIM2-1) or SEQ ID NO:6 (siPDLIM2-2)) or control oligonucleotides (Control), which were used in Example 1 or 2. After 2 days of culture, nuclear extract was prepared and immunoblotted with anti-PDLIM2 antibody. Anti-Sp-1 antibody was used as a control.

Figure 9:
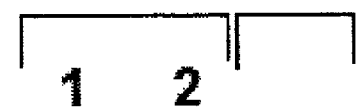
FIG. 9 shows immunoblot of nuclear extract of mouse embryonic fibroblasts using anti-PDLIM2 antibody. Mouse embryonic fibroblasts were transfected with siRNA against mouse PDLIM2 (SEQ ID NO:5 (siPDLIM2-1) or SEQ ID NO:6 (siPDLIM2-2)) or control oligonucleotides (Control). Anti-Sp-1 antibody was used as a control.
Figure 9:
Figure 9:

As shown in FIG. 9, both of siPDLIM2-1 and siPDLIM2-2 suppressed expression of PDLIM2 to a similar extent.

INDUSTRIAL APPLICABILITY

According to the present invention, a therapeutic agent for wound based on a novel mechanism not present heretofore, which includes suppression of the expression or function of PDLIM2, and a screening method therefor can be provided.

The invention claimed is:

1. A method for treating wounds in a human, which method comprises administering an effective amount of a substance that suppresses the expression or function of PDLIM2 to the human, wherein the substance is (a) an siRNA or antisense nucleic acid that specifically suppresses the expression of PDLIM2, wherein PDLIM2 comprises SEQ ID NO: 2, or (b) an expression vector that expresses the siRNA or antisense nucleic acid, such that the wounds in the human are treated.

2. The method of claim 1, wherein the substance is siRNA.

3. The method of claim 2, wherein the siRNA comprises SEQ ID NO: 7.

4. The method of claim 1, wherein the substance is an expression vector that expresses the siRNA.

5. The method of claim 4, wherein the siRNA comprises SEQ ID NO: 7.

6. The method of claim 1, wherein the substance is an antisense nucleic acid.

7. The method of claim 1, wherein the substance is an expression vector that expresses the antisense nucleic acid.

* * * * *